(12) United States Patent
Ikeda et al.

(10) Patent No.: US 11,510,640 B2
(45) Date of Patent: Nov. 29, 2022

(54) RADIOGRAPHY APPARATUS AND METHOD FOR CONTROLLING RADIOGRAPHY APPARATUS

(71) Applicant: FUJIFILM Corporation, Tokyo (JP)

(72) Inventors: Yuji Ikeda, Kanagawa (JP); Ryo Imamura, Kanagawa (JP); Shinichi Kano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 157 days.

(21) Appl. No.: 17/034,872

(22) Filed: Sep. 28, 2020

(65) Prior Publication Data

US 2021/0093269 A1    Apr. 1, 2021

(30) Foreign Application Priority Data

Sep. 30, 2019    (JP) .............................. JP2019-179765

(51) Int. Cl.
*A61B 6/00*    (2006.01)

(52) U.S. Cl.
CPC .......... *A61B 6/4441* (2013.01); *A61B 6/4085* (2013.01); *A61B 6/461* (2013.01); *A61B 6/54* (2013.01)

(58) Field of Classification Search
CPC ........... A61B 6/42; A61B 6/54; A61B 6/5205; A61B 6/485; A61B 6/5211; A61B 6/542;
(Continued)

(56) References Cited

U.S. PATENT DOCUMENTS

| 6,325,537 B1 | 12/2001 | Watanabe |
| 2003/0194056 A1 | 10/2003 | Spahn |

(Continued)

FOREIGN PATENT DOCUMENTS

| DE | 10 2004 022 804 B3 | 9/2005 |
| EP | 1 847 220 A2 | 10/2007 |

(Continued)

OTHER PUBLICATIONS

The extended European search report issued by the European Patent Office dated Feb. 12, 2021, which corresponds to European Patent Application No. 20198780.7-1126 and is related to U.S. Appl. No. 17/034,872.

(Continued)

*Primary Examiner* — Don K Wong
(74) *Attorney, Agent, or Firm* — Studebaker & Brackett PC

(57) ABSTRACT

The radiography apparatus includes: an irradiation unit having an irradiation opening through which radiation is emitted; an image receiving unit that has an image receiving surface receiving the radiation emitted from the irradiation unit; an arm that has one end at which the irradiation unit is rotatably supported and the other end at which the image receiving unit is supported in a posture in which the irradiation opening and the image receiving surface face each other; a solenoid that locks the rotation of the irradiation unit with respect to the arm in a facing posture in which the irradiation opening and the image receiving surface face each other; and a control unit that permits the moving image capture irradiation in a state in which the rotation of the irradiation unit is locked and prohibits the moving image capture irradiation in a state in which the rotation is unlocked.

11 Claims, 21 Drawing Sheets

(58) Field of Classification Search
CPC ........... A61B 6/548; A61B 6/56; A61B 6/461; A61B 6/4233; A61B 6/507; H05G 1/60; H05G 1/58; G01N 23/04
See application file for complete search history.

(56) References Cited

U.S. PATENT DOCUMENTS

| | | | |
|---|---|---|---|
| 2008/0011958 | A1 | 1/2008 | Endo et al. |
| 2008/0042312 | A1 | 2/2008 | Chen et al. |
| 2008/0317215 | A1 | 12/2008 | Takekoshi et al. |
| 2009/0010394 | A1 | 1/2009 | Watanabe |
| 2009/0103685 | A1 | 4/2009 | Abe et al. |
| 2011/0170669 | A1 | 7/2011 | Nakatsugawa et al. |
| 2012/0201351 | A1 | 8/2012 | Iwakiri et al. |
| 2014/0037058 | A1 | 2/2014 | Allen et al. |
| 2015/0069256 | A1 | 3/2015 | Nakata et al. |
| 2017/0303879 | A1 | 10/2017 | Maack |
| 2019/0282196 | A1* | 9/2019 | Tezuka .................. G01T 3/006 |

FOREIGN PATENT DOCUMENTS

| | | |
|---|---|---|
| JP | 2000-116631 A | 4/2000 |
| JP | 2001-037747 A | 2/2001 |
| JP | 2003-310591 A | 11/2003 |
| JP | 2005-000470 A | 1/2005 |
| JP | 2005-013431 A | 1/2005 |
| JP | 2007-289281 A | 11/2007 |
| JP | 2008-007923 A | 1/2008 |
| JP | 2009-000252 A | 1/2009 |
| JP | 2009-011466 A | 1/2009 |
| JP | 2009-050379 A | 3/2009 |
| JP | 2009-100947 A | 5/2009 |
| JP | 2009-195581 A | 9/2009 |
| JP | 2011-139851 A | 7/2011 |
| JP | 2012-161530 A | 8/2012 |
| JP | 2012-231905 A | 11/2012 |
| JP | 2015-054117 A | 3/2015 |
| JP | 2015-156896 A | 9/2015 |
| JP | 2017-086628 A | 5/2017 |
| JP | 2017-538457 A | 12/2017 |

OTHER PUBLICATIONS

"Notice of Reasons for Refusal" Office Action issued in JP 2019-179765; mailed by the Japanese Patent Office dated Jun. 28, 2022.

* cited by examiner

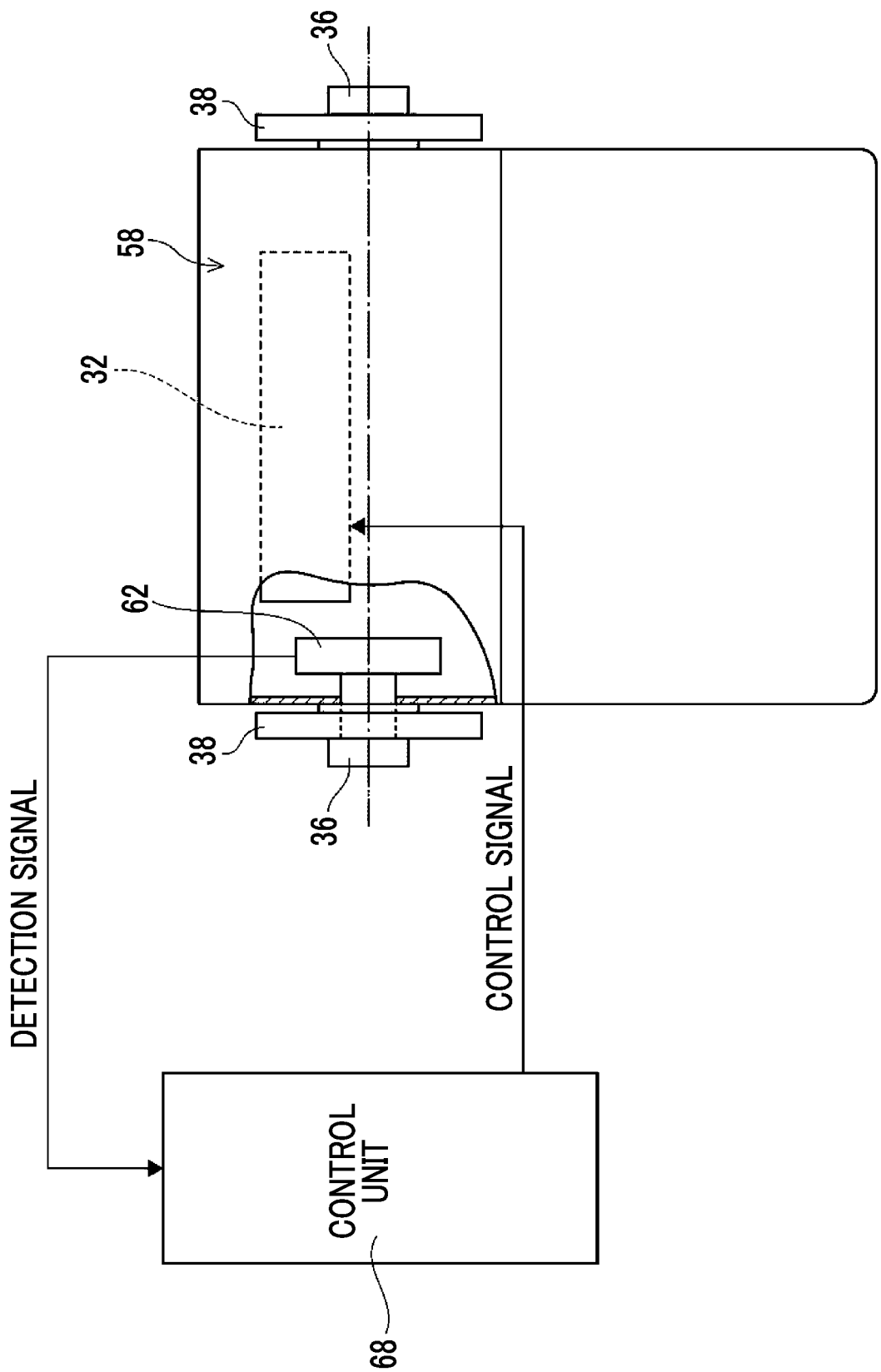

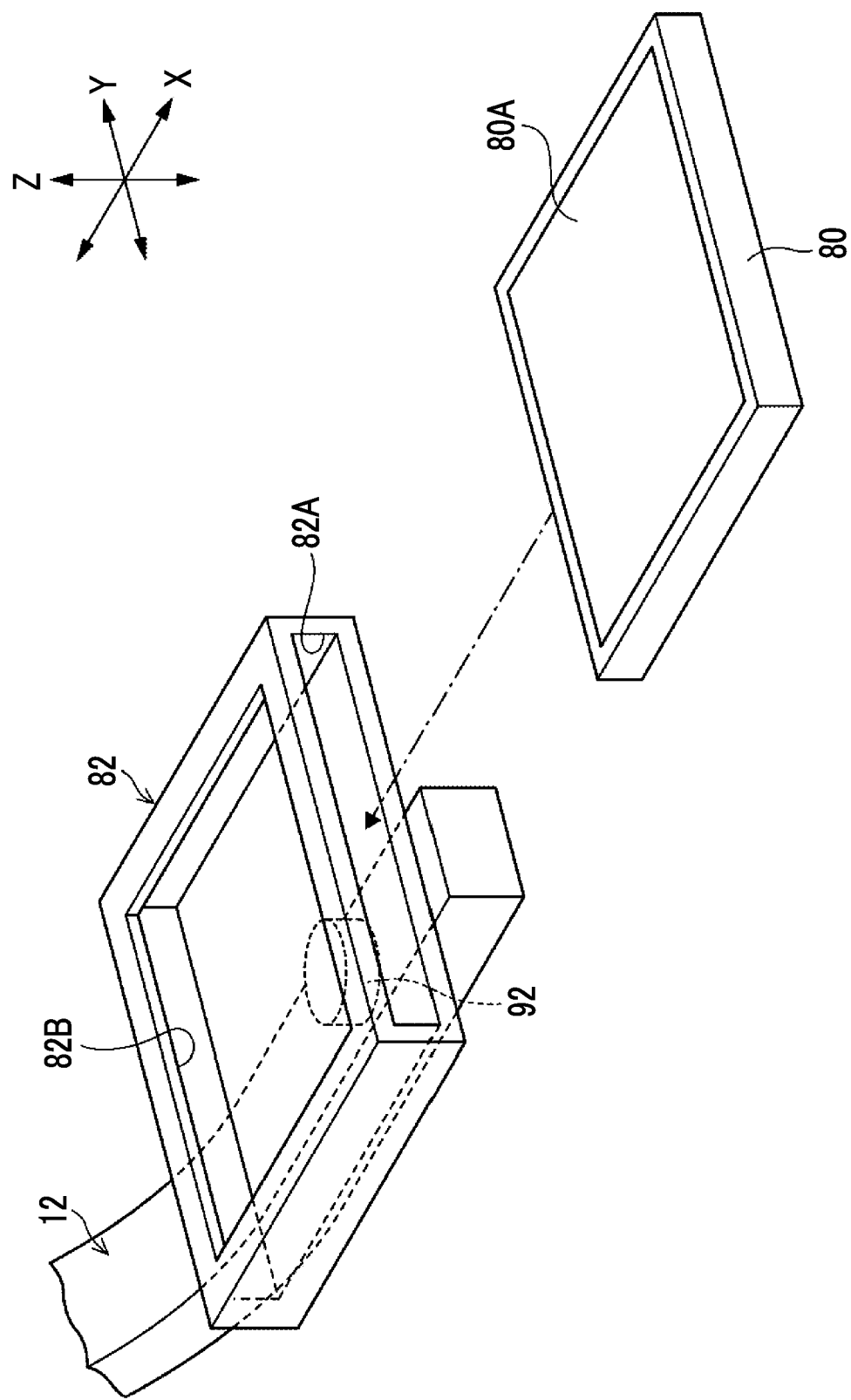

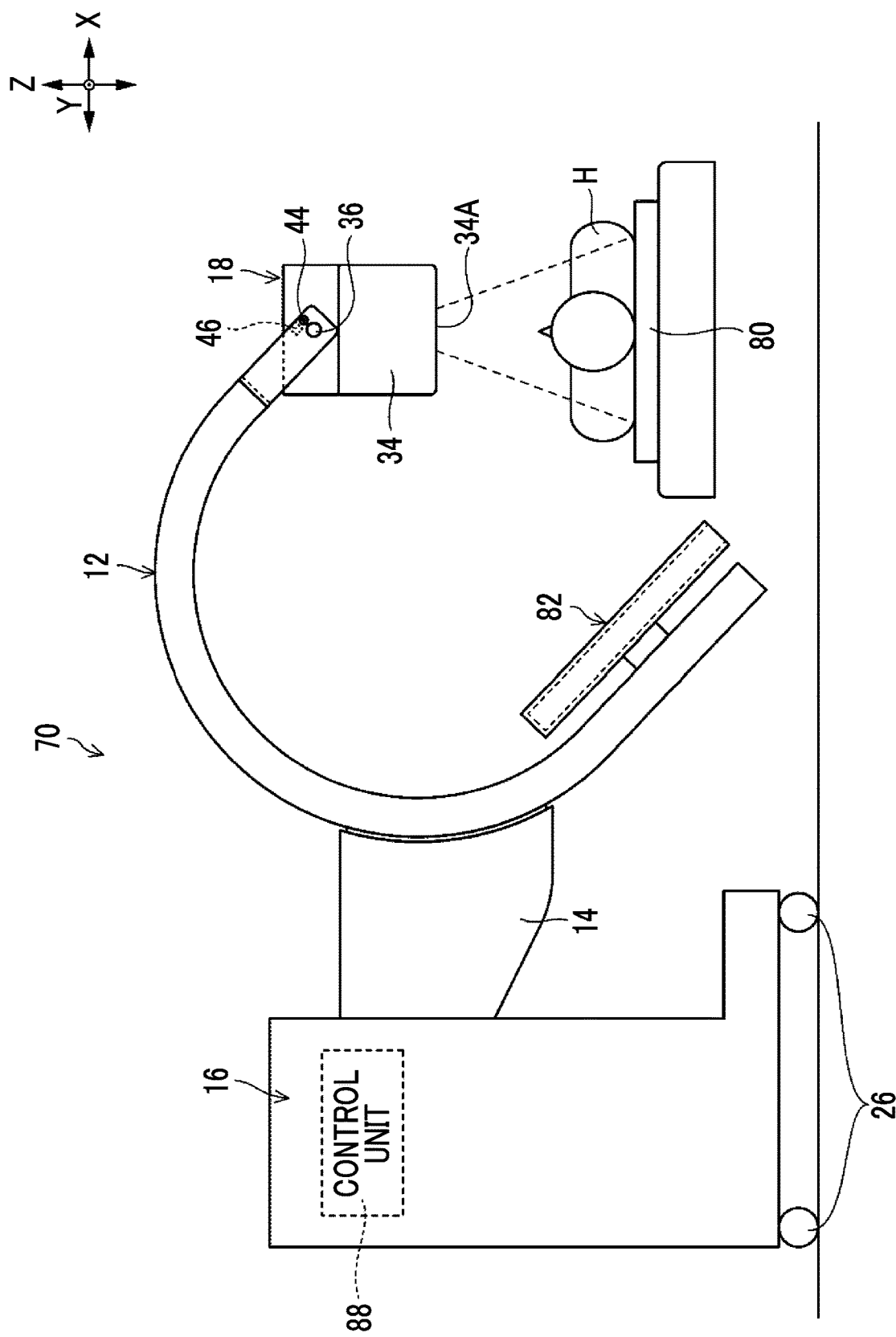

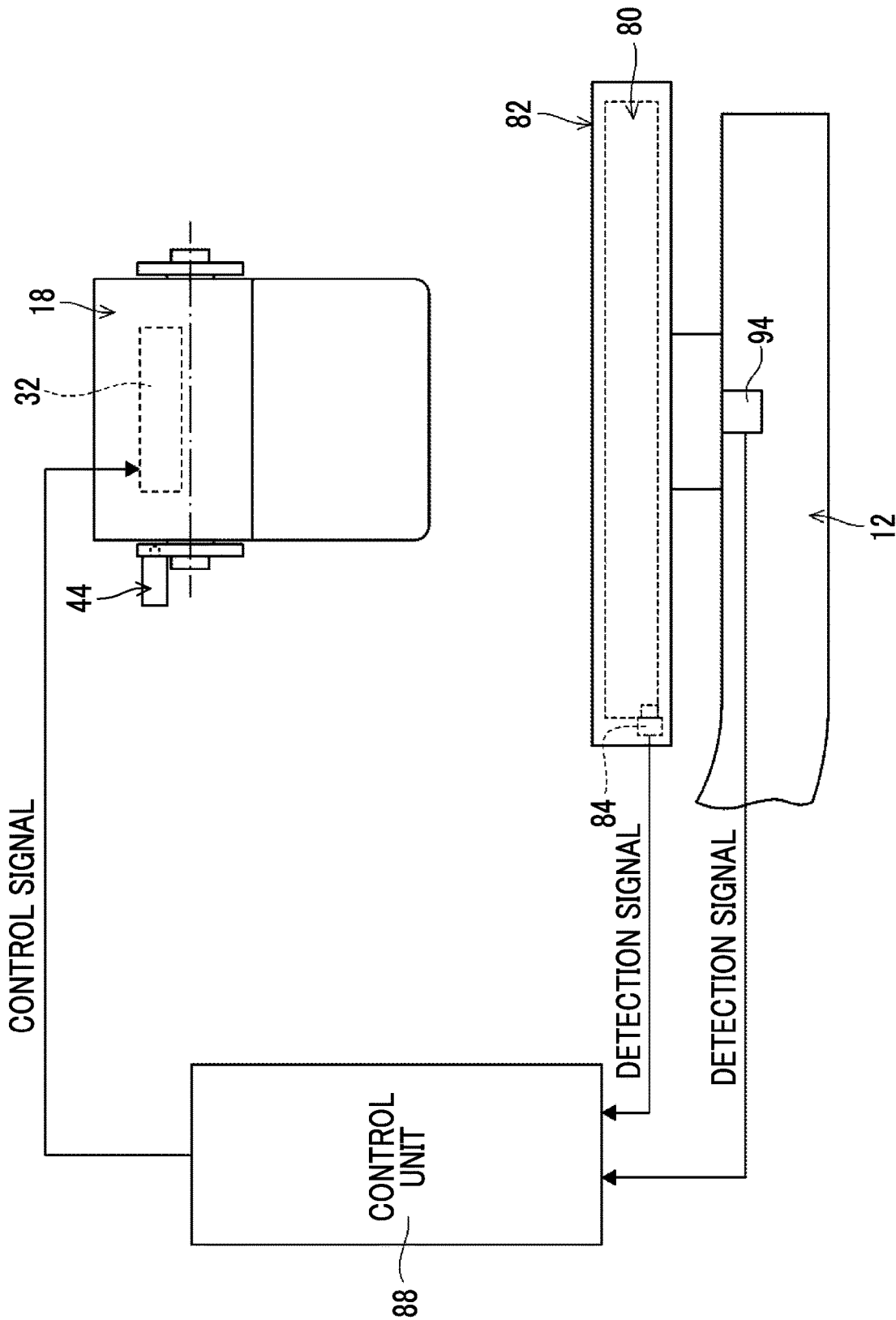

RADIOGRAPHY APPARATUS AND METHOD FOR CONTROLLING RADIOGRAPHY APPARATUS

CROSS-REFERENCE TO RELATED APPLICATIONS

The present application claims priority under 35 U.S.C. § 119 to Japanese Patent Application No., 2019-179765 filed on Sep. 30, 2019. The above application is hereby expressly incorporated by reference, in its entirety, into the present application.

BACKGROUND

1. Technical Field

The present disclosure relates to a radiography apparatus and a method for controlling a radiography apparatus.

2. Description of the Related Art

A radiography apparatus has been known which comprises an arm having one end at which an irradiation unit emitting radiation is provided. Among radiography apparatuses, a radiography apparatus has been known which includes an arm that has two ends and can support an image receiving unit at the other end in a posture in which the image receiving unit faces an irradiation unit provided at one end (See JP2005-000470A). The image receiving unit has an image receiving surface that receives radiation transmitted through a subject and outputs a radiographic image of the subject.

The radiography apparatus disclosed in JP2005-000470A comprises an arm (referred to as a C-arm or the like) having a C-shape in a side view. The arm is positioned such that the subject is interposed between the irradiation unit and the image receiving unit. Further, in the radiography apparatus disclosed in JP2005-000470A, the irradiation unit is attached to one end of the arm so as to be rotatable with respect to the arm. Therefore, the irradiation direction of the irradiation unit can be changed. As a result, for example, it is possible to adjust the irradiation direction of the irradiation unit according to the position or imaging part of the subject.

SUMMARY

In a case in which a moving image (also referred to as a fluoroscopic image) of the subject is captured by the radiography apparatus disclosed in JP2005-000470A, radiation is continuously emitted from the irradiation unit. However, in a case in which the radiography apparatus has the moving image capture function and the above-mentioned function of adjusting the irradiation direction of the irradiation unit, there are the following problems.

That is, in the case of the capture of a moving image, radiation is continuously emitted for a relatively long time. Therefore, in a case in which a moving image is captured in a state in which the irradiation opening of the irradiation unit through which radiation is emitted and the image receiving surface of the image receiving unit do not face each other, unnecessary radiation that does not contribute to the capture of a moving image may be continuously emitted. This problem is expected to be improved especially in the capture of a moving image, unlike the case of the capture of a still image in which the emission of radiation is completed in a short time.

An object of the technology of the present disclosure is to provide a radiography apparatus and a method for controlling a radiography apparatus which can suppress the emission of unnecessary radiation that does not contribute to the capture of a moving image.

According to a first aspect of the present disclosure, there is provided a radiography apparatus comprising: an irradiation unit having an irradiation opening through which radiation is emitted; an image receiving unit that has an image receiving surface receiving the radiation, which has been emitted from the irradiation unit and transmitted through a subject, and outputs a radiographic image of the subject; an arm that has one end at which the irradiation unit is provided and the other end at which the image receiving unit is capable of being supported in a posture in which the irradiation opening of the irradiation unit and the image receiving surface face each other and supports the irradiation unit so as to be rotatable in a direction in which orientation of the irradiation opening with respect to the image receiving surface is changed; a locking mechanism that locks rotation of the irradiation unit with respect to the arm in a facing posture in which the irradiation opening and the image receiving surface face each other; and a control unit that is capable of directing the irradiation unit to perform moving image capture irradiation in which the irradiation unit continuously emits the radiation to capture a moving image of the subject, permits the moving image capture irradiation in a state in which the rotation of the irradiation unit is locked by the locking mechanism, and prohibits the moving image capture irradiation in a state in which the rotation is unlocked by the locking mechanism.

According to the above configuration, the radiography apparatus comprises: the locking mechanism that locks the rotation of the irradiation unit with respect to the arm at the position where the irradiation opening faces the image receiving surface; and the control unit that prohibits the moving image capture irradiation in a state in which the rotation of the irradiation unit is unlocked. Therefore, it is possible to suppress the emission of unnecessary radiation that does not contribute to the capture of a moving image.

According to a second aspect of the present disclosure, there is provided a radiography apparatus comprising: an irradiation unit having an irradiation opening through which radiation is emitted; an image receiving unit that has an image receiving surface receiving the radiation, which has been emitted from the irradiation unit and transmitted through a subject, and outputs a radiographic image of the subject; an arm that has one end at which the irradiation unit is provided and the other end at which the image receiving unit is capable of being supported in a posture in which the irradiation opening of the irradiation unit and the image receiving surface face each other and supports the irradiation unit so as to be rotatable in a direction in which orientation of the irradiation opening with respect to the image receiving surface is changed; a posture detection unit that detects whether or not the irradiation opening is in a facing posture in which the irradiation opening faces the image receiving surface; and a control unit that is capable of directing the irradiation unit to perform moving image capture irradiation in which the irradiation unit continuously emits the radiation to capture a moving image of the subject, permits the moving image capture irradiation in a state in which the posture detection unit detects that the irradiation opening is in the facing posture, and prohibits the moving image capture irradiation in a state in which the posture detection unit does not detect that the irradiation opening is in the facing posture.

According to the above configuration, the radiography apparatus comprises: the posture detection unit that detects whether or not the irradiation opening is in the facing posture in which the irradiation opening faces the image receiving surface; and the control unit that prohibits the moving image capture irradiation in a state in which the posture detection unit does not detect that the irradiation opening is in the facing posture. Therefore, it is possible to suppress the emission of unnecessary radiation that does not contribute to the capture of a moving image.

According to a third aspect of the present disclosure, in the radiography apparatus according to the first or second aspect, the facing posture may be a confronting posture in which a central axis of a beam of the radiation that spreads in a cone shape from a focus of the irradiation unit through the irradiation opening is aligned with a normal line to the image receiving surface.

According to the above configuration, the moving image capture irradiation is prohibited in postures other than the confronting posture. Therefore, it is possible to further suppress the emission of unnecessary radiation that does not contribute to the capture of a moving image.

According to a fourth aspect of the present disclosure, in the radiography apparatus according to any one of the first to third aspects, in a case in which a direction in which the irradiation unit and the image receiving unit are provided with respect to the arm is a front side and an arm side is a rear side in a side view of the arm, the irradiation unit may be rotated with respect to the arm such that the orientation of the irradiation opening is changed in a front-rear direction.

According to the above configuration, the orientation of the irradiation opening of the irradiation unit is rotated in the front-rear direction with respect to the arm. Therefore, it is possible to adjust the orientation of the irradiation opening without moving the arm.

According to a fifth aspect of the present disclosure, in the radiography apparatus according to any one of the first to fourth aspects, control to prohibit the moving image capture irradiation by the control unit may include at least one of control to prohibit a start of the moving image capture irradiation in a case in which there is a command to start the moving image capture irradiation or control to stop the moving image capture irradiation while the moving image is being captured.

According to the above configuration, the start of the moving image capture irradiation is prohibited while the moving image is not being captured or the moving image capture irradiation is stopped while the moving image is being captured. Therefore, it is possible to suppress the emission of unnecessary radiation that does not contribute to the capture of a moving image.

According to a sixth aspect of the present disclosure, the radiography apparatus according to the fifth aspect may further comprise a warning unit that issues a warning in at least one of a case in which the control unit prohibits the start of the moving image capture irradiation or a case in which the control unit stops the moving image capture irradiation while the moving image is being captured.

According to the above configuration, a warning is issued in a case in which the start of the moving image capture irradiation is prohibited or in a case in which the moving image capture irradiation is stopped. Therefore, it is possible to inform the operator that the capture of the moving image has been prohibited or that the capture of the moving image has been stopped.

According to a seventh aspect of the present disclosure, in the radiography apparatus according to any one of the first to sixth aspects, the control unit may be capable of directing the irradiation unit to perform still image capture irradiation in which the irradiation unit emits the radiation for a shorter time than in the moving image capture irradiation to capture a still image of the subject, in addition to the moving image capture irradiation. The control unit may permit the still image capture irradiation even in a case in which the moving image capture irradiation is prohibited.

Unlike the capture of a moving image, in the capture of a still image, in many cases, the irradiation direction of the irradiation unit is changed to various directions and the irradiation unit is used. For example, in a case in which the image receiving unit is attachable to and detachable from the arm, the image receiving unit may be detached from the arm for capturing a still image. In that case, it is necessary to change the irradiation direction of the irradiation unit according to the position where the image receiving unit is provided.

According to the above configuration, even in a case in which the moving image capture irradiation is prohibited, the still image capture irradiation is permitted. Therefore, it is possible to change the irradiation direction of the irradiation unit to various directions and to capture still images. As a result, it is possible to improve convenience.

According to an eighth aspect of the present disclosure, in the radiography apparatus according to any one of the first to seventh aspects, the image receiving unit may be attachable to and detachable from the arm. The radiography apparatus may further comprise an attachment and detachment detection unit that detects whether or not the image receiving unit is detached from the arm. The control unit may prohibit the irradiation unit from performing the moving image capture irradiation in a state in which the image receiving unit is detached from the arm, regardless of whether or not the rotation of the irradiation unit by the locking mechanism is locked or whether or not the posture detection unit detects that the irradiation opening is in the facing posture.

According to the above configuration, the moving image capture irradiation is prohibited in a state in which the image receiving unit is detached from the arm, regardless of whether or not the rotation of the irradiation unit is locked or whether or not the irradiation opening is in the facing posture. Therefore, it is possible to suppress the emission of unnecessary radiation that does not contribute to the capture of a moving image.

According to a ninth aspect of the present disclosure, in the radiography apparatus according to any one of the fourth to eighth aspects citing the third aspect, each of the irradiation opening and the image receiving surface may have a rectangular shape. The image receiving unit may be rotatable with respect to the arm while maintaining the confronting posture. The radiography apparatus may further comprise a rotational position detection unit that detects at least four rotational positions of the image receiving unit where, in a case in which the irradiation opening is projected onto the image receiving surface, four sides of the irradiation opening are parallel to corresponding four sides of the image receiving surface. The at least four rotational positions may be set at intervals of 90°. The control unit may prohibit the irradiation unit from performing the moving image capture irradiation in a case in which the image receiving unit is at a rotational position other than the four rotational positions, regardless of whether or not the rotation of the irradiation unit by the locking mechanism is locked or whether or not the posture detection unit detects that the irradiation opening is in the confronting posture.

According to the above configuration, the moving image capture irradiation is prohibited in a case in which the image receiving unit is at a rotational position other than the four rotational positions, regardless of whether or not the rotation of the irradiation unit is locked or whether or not the irradiation opening is in the confronting posture. Therefore, it is possible to suppress the emission of unnecessary radiation that does not contribute to the capture of a moving image.

According to a tenth aspect of the present disclosure, there is provided a method for controlling a radiography apparatus comprising an irradiation unit having an irradiation opening through which radiation is emitted, an image receiving unit that has an image receiving surface receiving the radiation, which has been emitted from the irradiation unit and transmitted through a subject, and outputs a radiographic image of the subject, an arm that has one end at which the irradiation unit is provided and the other end at which the image receiving unit is capable of being supported in a posture in which the irradiation opening of the irradiation unit and the image receiving surface face each other and supports the irradiation unit so as to be rotatable in a direction in which orientation of the irradiation opening with respect to the image receiving surface is changed, and a control unit that is capable of directing the irradiation unit to perform moving image capture irradiation in which the irradiation unit continuously emits the radiation to capture a moving image of the subject. The method comprises allowing the control unit to perform at least one of first control to permit the moving image capture irradiation in a state in which rotation of the irradiation unit is locked by a locking mechanism that locks the rotation of the irradiation unit with respect to the arm in a facing posture in which the irradiation opening and the image receiving surface face each other and to prohibit the moving image capture irradiation in a state in which the rotation is unlocked by the locking mechanism or second control to permit the moving image capture irradiation in a state in which a posture detection unit that detects whether or not the irradiation opening is in a facing posture in which the irradiation opening faces the image receiving surface detects that the irradiation opening is in the facing posture and to prohibit the moving image capture irradiation in a state in which the posture detection unit does not detect that the irradiation opening is in the facing posture.

According to the above configuration, in the first control, the moving image capture irradiation is permitted in a state in which the rotation of the irradiation unit is locked by the locking mechanism in the facing posture in which the irradiation opening and the image receiving surface face each other. The moving image capture irradiation is prohibited in a state in which the rotation is unlocked by the locking mechanism.

In the second control, the moving image capture irradiation is permitted in a state in which the posture detection unit detects that the irradiation opening is in the facing posture. The moving image capture irradiation is prohibited in a state in which the posture detection unit does not detect that the irradiation opening is in the facing posture. The control unit performs at least one of the first control or the second control to suppress the emission of unnecessary radiation that does not contribute to the capture of a moving image.

According to the technology of the present disclosure, it is possible to suppress the emission of unnecessary radiation that does not contribute to the capture of a moving image.

BRIEF DESCRIPTION OF THE DRAWINGS

Exemplary embodiments according to the technique of the present disclosure will be described in detail based on the following figures, wherein:

FIG. 10 is a block diagram illustrating a functional configuration of a control unit of the radiography apparatus according to the second embodiment;

FIG. 11 is a partial perspective view illustrating an image receiving unit of a radiography apparatus according to a third embodiment;

FIG. 14 is an overall side view illustrating an aspect of the use of the radiography apparatus according to the third embodiment;

FIG. 15 is a block diagram illustrating a functional configuration of a control unit of the radiography apparatus according to the third embodiment.

DETAILED DESCRIPTION

Figure 1:
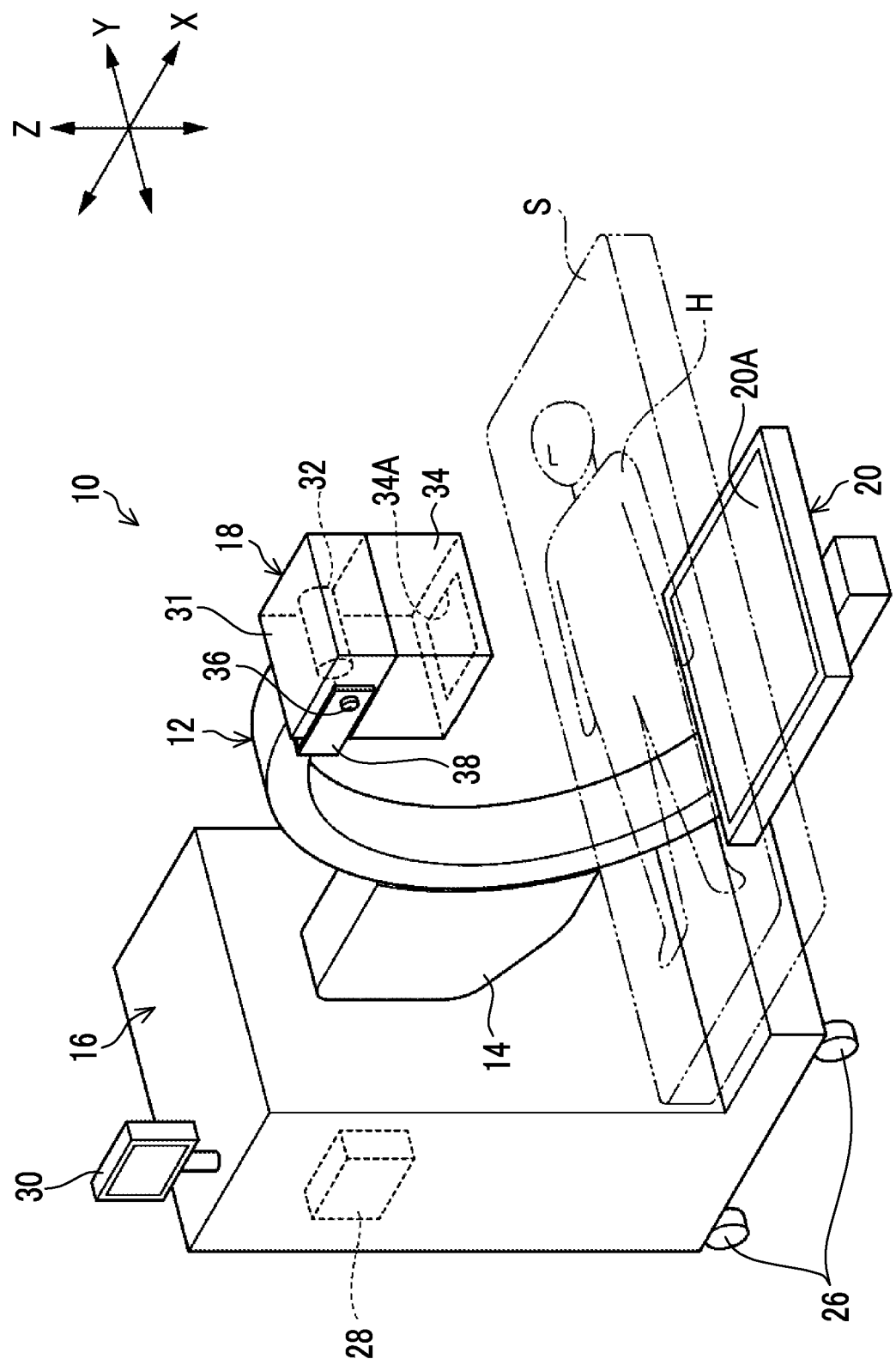
FIG. 1 is an overall perspective view illustrating a radiography apparatus according to a first embodiment.

Hereinafter, radiography apparatuses according to first to third embodiments of the present disclosure will be sequentially described with reference to the drawings. In the drawings, an arrow X indicates the front-rear direction of the radiography apparatus, an arrow Y indicates the width direction of the radiography apparatus, and an arrow Z indicates the vertical direction.

First Embodiment

First, a radiography apparatus according to the first embodiment of the present disclosure will be described with reference to FIGS. 1 to 7.

Overall Configuration of Radiography Apparatus

A radiography apparatus 10 according to this embodiment illustrated in FIG. 1 is an apparatus that captures a radiographic image of a subject H. The radiography apparatus 10 can capture, for example, moving images and still images of the subject H. The capture of the moving image is performed, for example, in a case in which a treatment target part of the subject H is displayed as a moving image during surgery (also referred to as fluoroscopy). In the capture of the moving image, for example, the moving image of the subject H is displayed on a monitor (not illustrated) that is provided separately from the radiography apparatus 10. Of course, data of the captured moving image may be stored in a memory of the radiography apparatus 10. In addition, in the case of the capture of the still image, the captured still image may be displayed on the monitor or may be stored in the memory of the radiography apparatus 10.

As illustrated in FIG. 1, the radiography apparatus 10 includes an arm 12 (referred to as a C-arm or the like) having a C-shape (an arc shape) in a side view and a main body 16 to which a support portion 14 is attached. In the following description, it is assumed that the side of the radiography apparatus 10 on which the arm 12 is provided is the front side of the radiography apparatus 10 and the side of the radiography apparatus 10 on which the main body 16 is provided is the rear side of the radiography apparatus 10.

Configuration of Arm

The arm 12 has two ends. An irradiation unit 18 is provided at one end of the arm 12 and an image receiving unit 20 is provided at the other end. The arm 12 can hold the irradiation unit 18 and the image receiving unit 20 in a posture in which they face each other. A space, into which the subject H and a bed S on which the subject H lies supine can be inserted, is ensured between the irradiation unit 18 and the image receiving unit 20. In the following description, in some cases, in a side view of the arm 12 (as viewed from the Y direction in FIG. 1), a direction in which the irradiation unit 18 and the image receiving unit 20 are provided is referred to as the front side of the arm 12 and the side of the support portion 14 is referred to as the rear side of the arm 12.

Figure 2A:
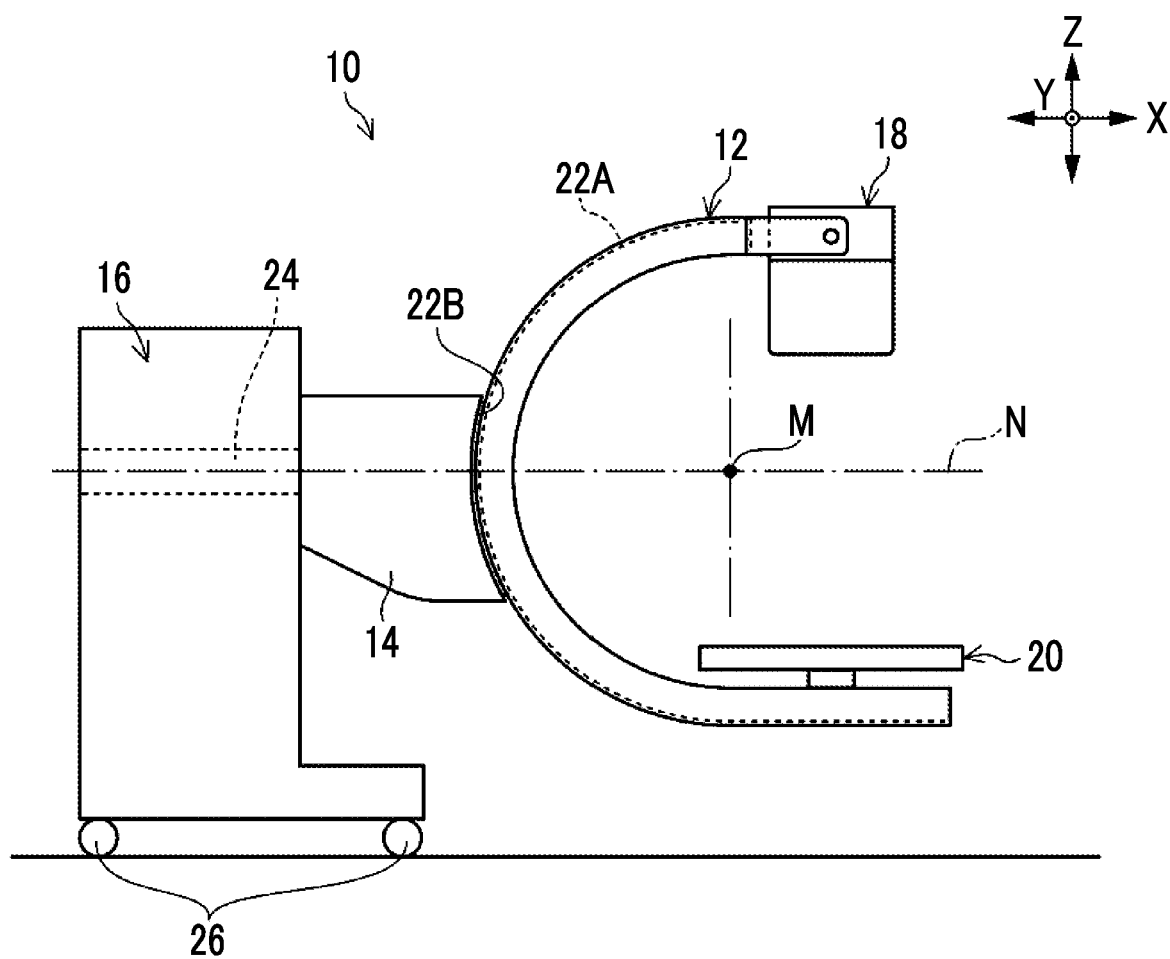
FIG. 2A is a side view illustrating the radiography apparatus according to the first embodiment.

Further, as illustrated in FIG. 2A, the arm 12 can be rotated about at least two different axis lines M (an axis line parallel to the Y axis) and N (an axis line parallel to the X axis) with respect to the main body 16. Specifically, a rail 22B is formed in the support portion 14. A rail fitting portion 22A that is fitted to the rail 22B is provided in an outer peripheral surface of the arm 12. The rail 22B has, for example, a groove shape and the rail fitting portion 22A having a convex shape is fitted to the rail 22B. The rail fitting portion 22A has an arc shape following the shape of the arm 12. The rail 22B also has an arc shape that has the same radius as the arc of the arm 12.

The rail fitting portion 22A formed on the arm 12 slides along the rail 22B formed on the support portion 14 such that the arm 12 can be orbitally rotated about the axis line M at the center of the arc of the arm 12 with respect to the support portion 14 and the main body 16.

Figure 2B:
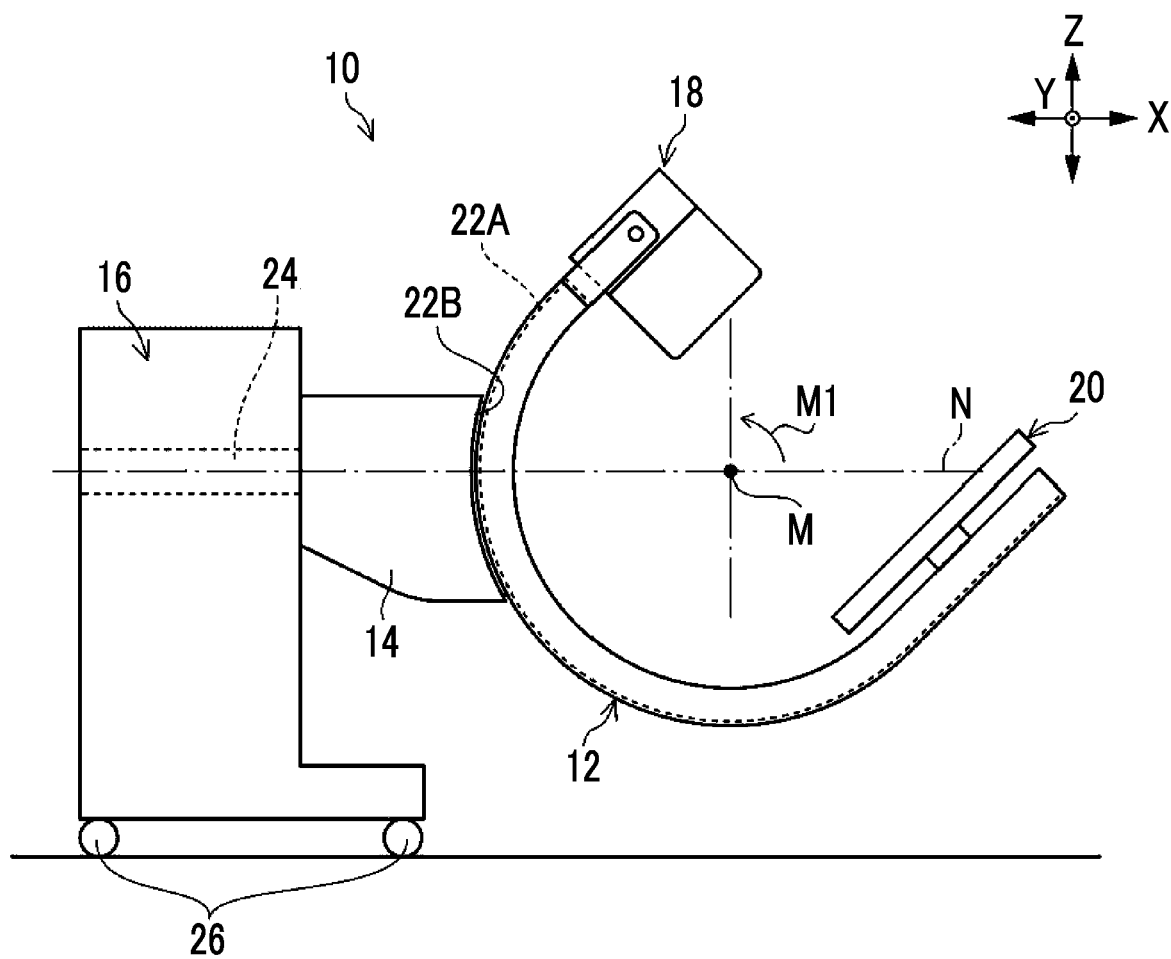
FIG. 2B is a side view illustrating a state in which an arm of the radiography apparatus illustrated in FIG. 2A is rotated in the direction of an arrow M1.
Figure 2C:
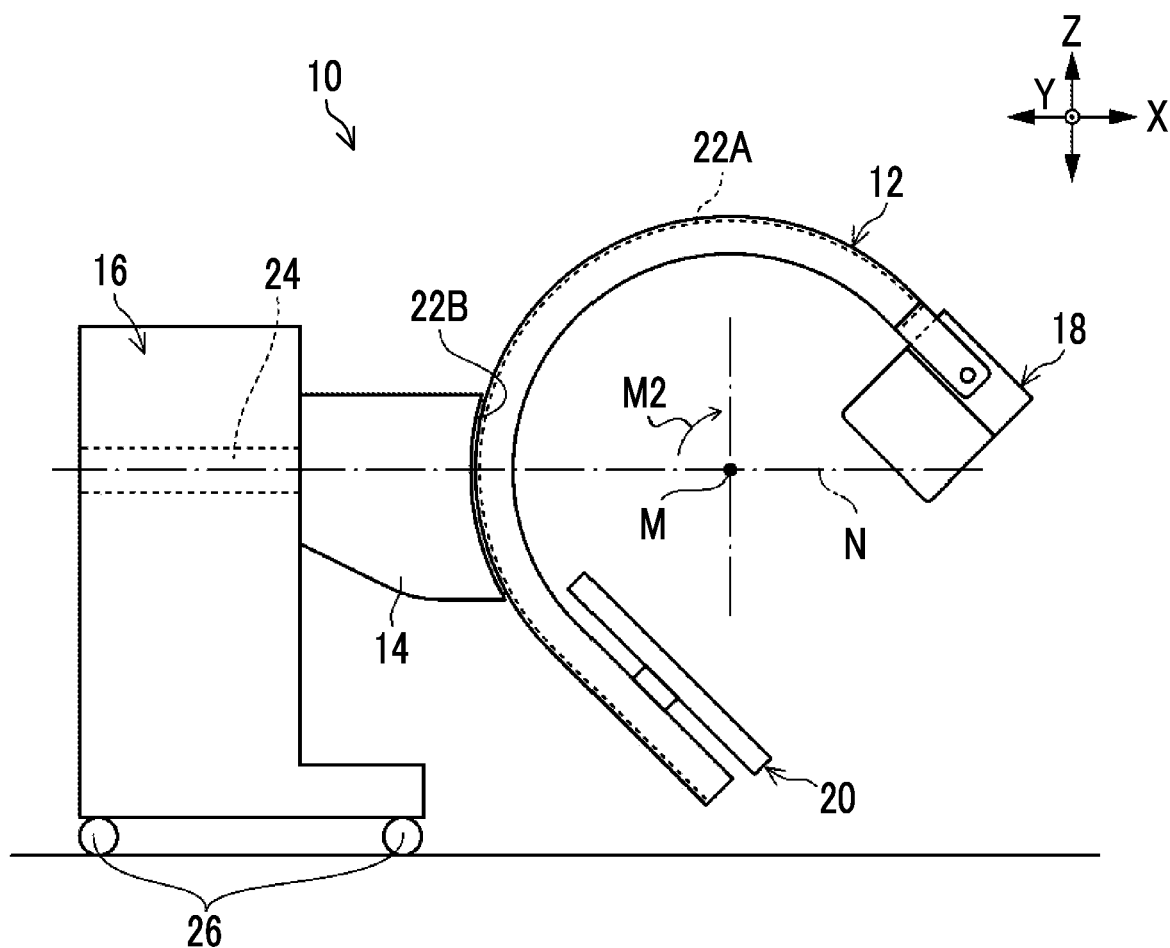
FIG. 2C is a side view illustrating a state in which the arm of the radiography apparatus illustrated in FIG. 2A is rotated in the direction of an arrow M2.

That is, as illustrated in FIGS. 2B and 2C, it is possible to orbitally rotate the arm 12 about the axis line M in the direction of an arrow M1 (counterclockwise in FIG. 2B) and the direction of an arrow M2 (clockwise in FIG. 2C). Therefore, it is possible to rotate the irradiation unit 18 and the image receiving unit 20 provided at both ends of the arm 12 about the body axis (an axis parallel to the Y axis) of the subject H (see FIG. 1).

The support portion 14 has a support shaft 24 that extends in the front-rear direction of the radiography apparatus 10 and the support shaft 24 is supported by the main body 16 through a bearing (not illustrated). Therefore, as illustrated in FIGS. 3A to 3C, the support portion 14 can be rotated about the axis line N of the support shaft 24 as a rotation center with respect to the main body 16 and the arm 12 can also be rotated about the axis line with respect to the main body 16 together with the support portion 14.

Figure 3A:
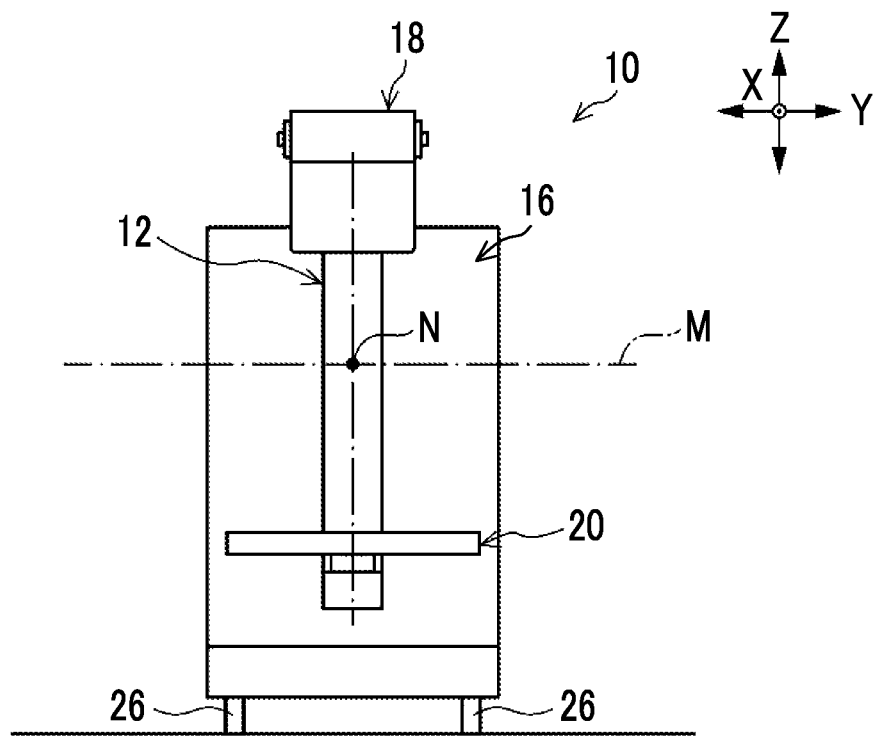
FIG. 3A is a front view illustrating the radiography apparatus according to the first embodiment.
Figure 3B:
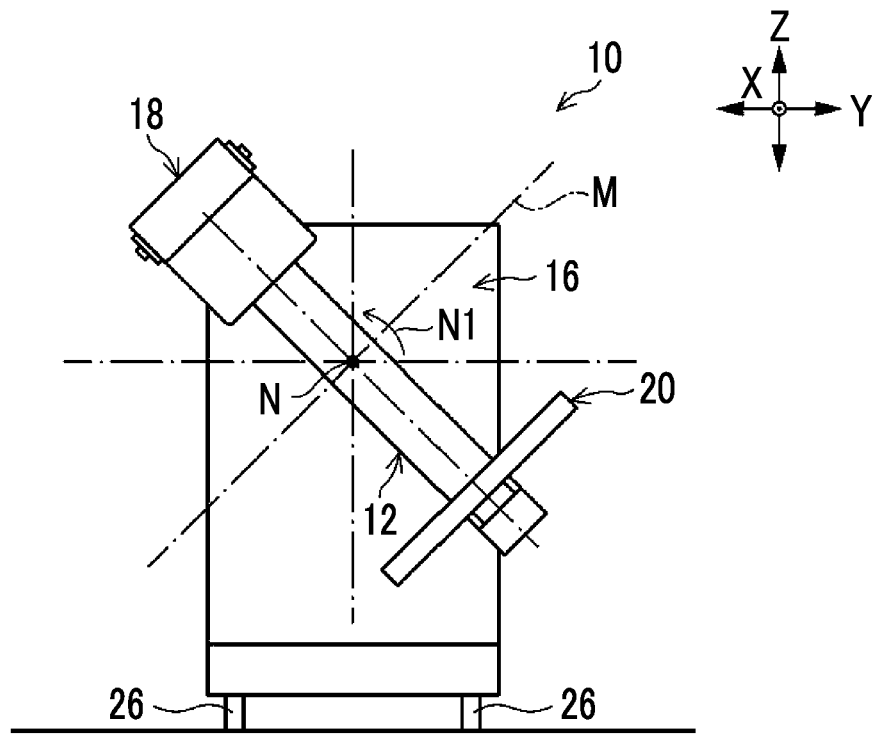
FIG. 3B is a front view illustrating a state in which the arm of the radiography apparatus illustrated in FIG. 3A is rotated in the direction of an arrow N1.
Figure 3C:
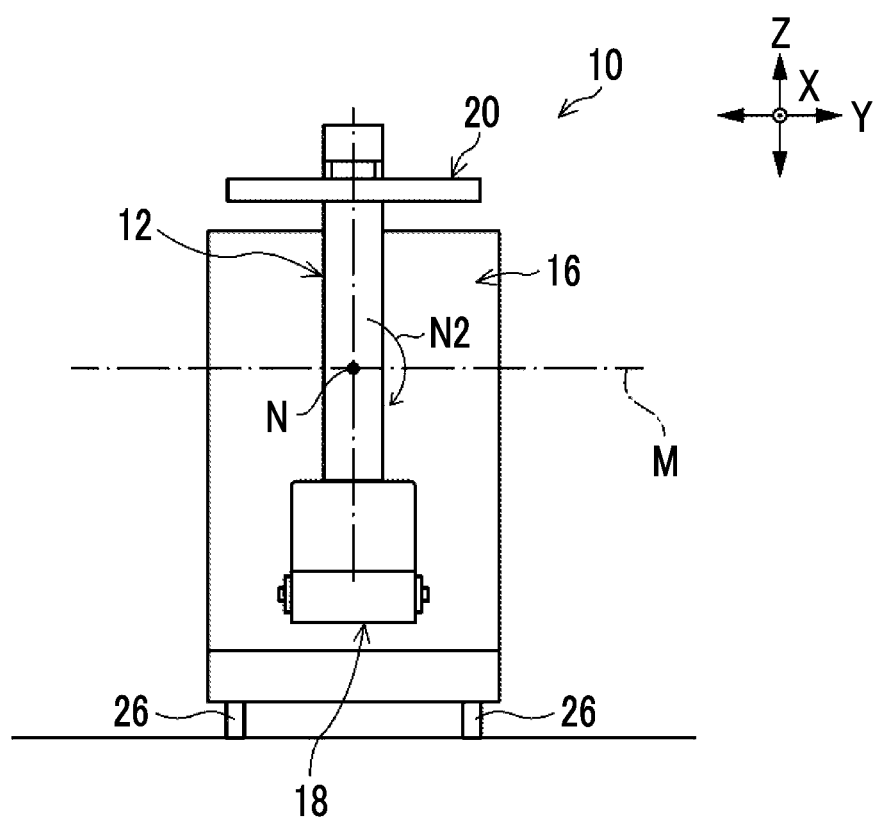
FIG. 3C is a front view illustrating a state in which the arm of the radiography apparatus illustrated in FIG. 3A is rotated 180° in the direction of an arrow N2.

That is, as illustrated in FIGS. 3B and 3C, it is possible to rotate the arm 12 about the axis line N in the direction of an arrow N1 (counterclockwise in FIG. 3B) and the direction of an arrow N2 (clockwise in FIG. 3C). Therefore, it is possible to reverse the positions of the irradiation unit 18 and the image receiving unit 20 provided at both ends of the arm 12 with respect to the subject H (see FIG. 1) in the vertical direction (Z-axis direction).

Here, the posture of the arm 12 in which the irradiation unit 18 is disposed above the image receiving unit 20 as illustrated in FIG. 3A is also referred to as an overtube posture since a radiation tube 32 (see FIG. 1) included in the irradiation unit 18 is located above the subject H. In contrast, the posture of the arm 12 in which the irradiation unit 18 is disposed below the image receiving unit 20 illustrated in FIG. 3C is referred to as an undertube posture since the radiation tube 32 is located below the subject H.

In the overtube posture, it is possible to increase a distance between the irradiation unit 18 and the subject H (see FIG. 1) and thus to capture an image of a relatively wide region, as compared to the undertube posture. Therefore, the overtube posture is mainly used to capture the still image of the subject H. In contrast, in the undertube posture, since the radiation emitted from the irradiation unit 18 is partially shielded by, for example, the bed S, it is possible to reduce the amount of radiation exposure of a surgeon or an operator (not illustrated) around the subject H (see FIG. 1). Therefore, the undertube posture is used for the capture of the moving image of the subject H in which radiation is continuously emitted.

Configuration of Main Body

As illustrated in FIG. 1, a plurality of casters 26 are attached to a lower portion of the main body 16 of the radiography apparatus 10 and the operator can push the radiography apparatus 10 with hands to move the radiography apparatus 10 into, for example, an operating room or a hospital ward. That is, the radiography apparatus 10 according to this embodiment is a mobile type.

Further, the main body 16 includes a control unit 28 that controls each unit of the radiography apparatus 10, such as the irradiation unit 18, and an operation panel 30 that is, for example, a touch panel type. The configuration of the control unit 28 will be described in detail below.

The operation panel 30 functions as an operation unit that inputs an operation command to each unit of the radiography apparatus 10, such as the irradiation unit 18, to operate each unit and a display unit that displays various kinds of information, such as a warning message and a radiographic image output from the image receiving unit 20. In addition, the main body 16 comprises various switches (not illustrated) including, for example, a power switch of the radiography apparatus 10, a power supply circuit that supplies power to each unit of the radiography apparatus 10, and a battery.

Configuration of Irradiation Unit

The irradiation unit 18 comprises a radiation source 31 and an irradiation field limiter 34. The radiation source 31 comprises the radiation tube 32 that generates radiation. The radiation is, for example, X-rays. The radiation tube 32 generates radiation by colliding electrons generated from a cathode with a target (anode). The position where the electrons collide with the target is a focus where radiation is emitted.

The irradiation field limiter 34 is provided below the radiation source 31. The irradiation field limiter 34 (also referred to as a collimator or the like) has a rectangular irradiation opening 34A. The radiation generated by the radiation tube 32 is emitted to the subject H through the irradiation opening 34A. The irradiation field limiter 34 can adjust the opening area of the irradiation opening 34A. The irradiation field limiter 34 has, for example, four shielding plates (not illustrated) that shield radiation. In each of the four shielding plates, each side corresponds to each side of the irradiation opening 34A and defines the irradiation opening 34A. The position of the shielding plates is changed to adjust the opening area of the irradiation opening 34A and the irradiation field of the radiation emitted from the irradiation unit 18 is changed.

Figure 4A:
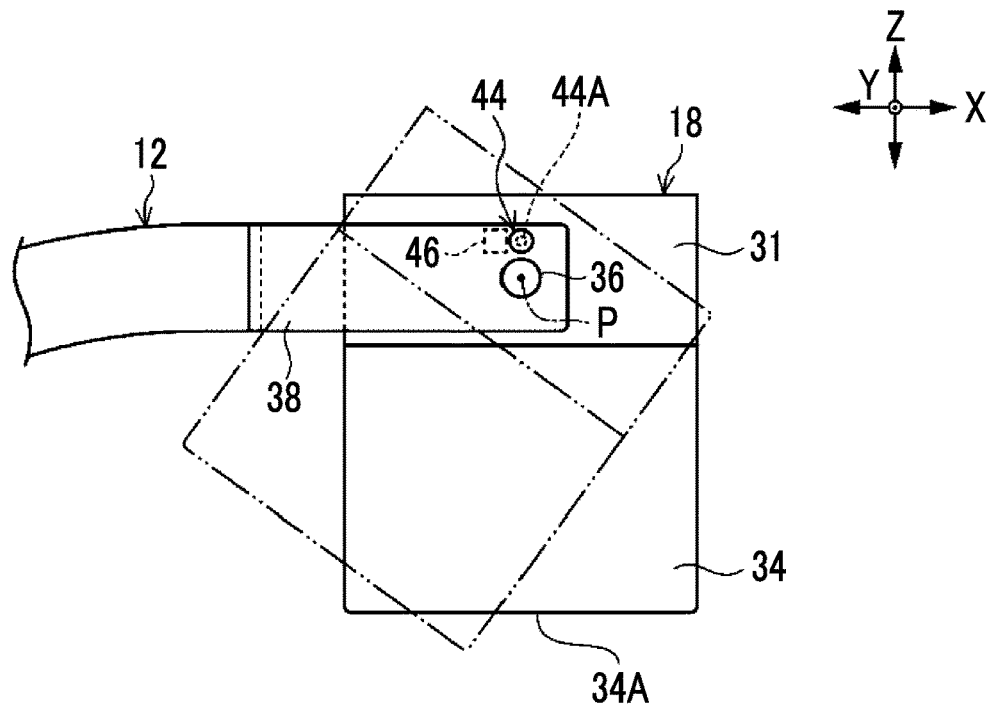
FIG. 4A is a partial side view illustrating an irradiation unit of the radiography apparatus according to the first embodiment.
Figure 4B:
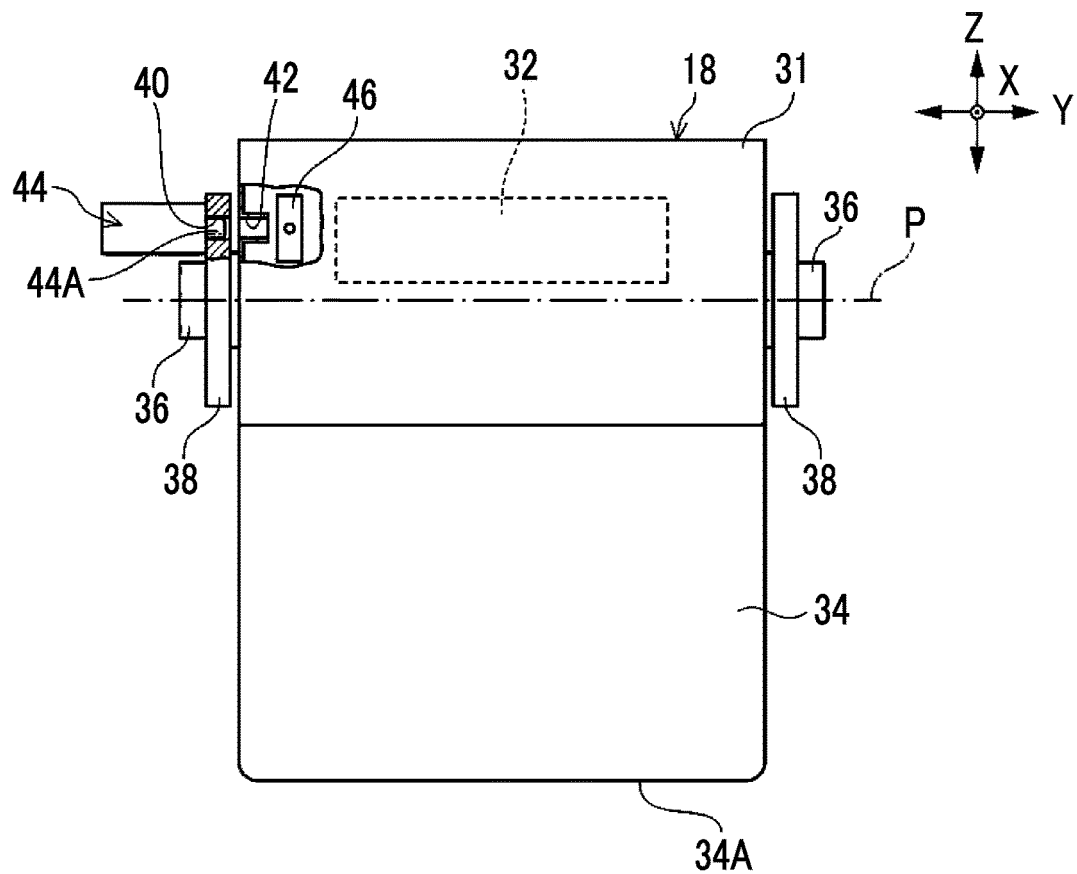
FIG. 4B is a front view illustrating an unlocked state of the irradiation unit illustrated in FIG. 4A.
Figure 4C:
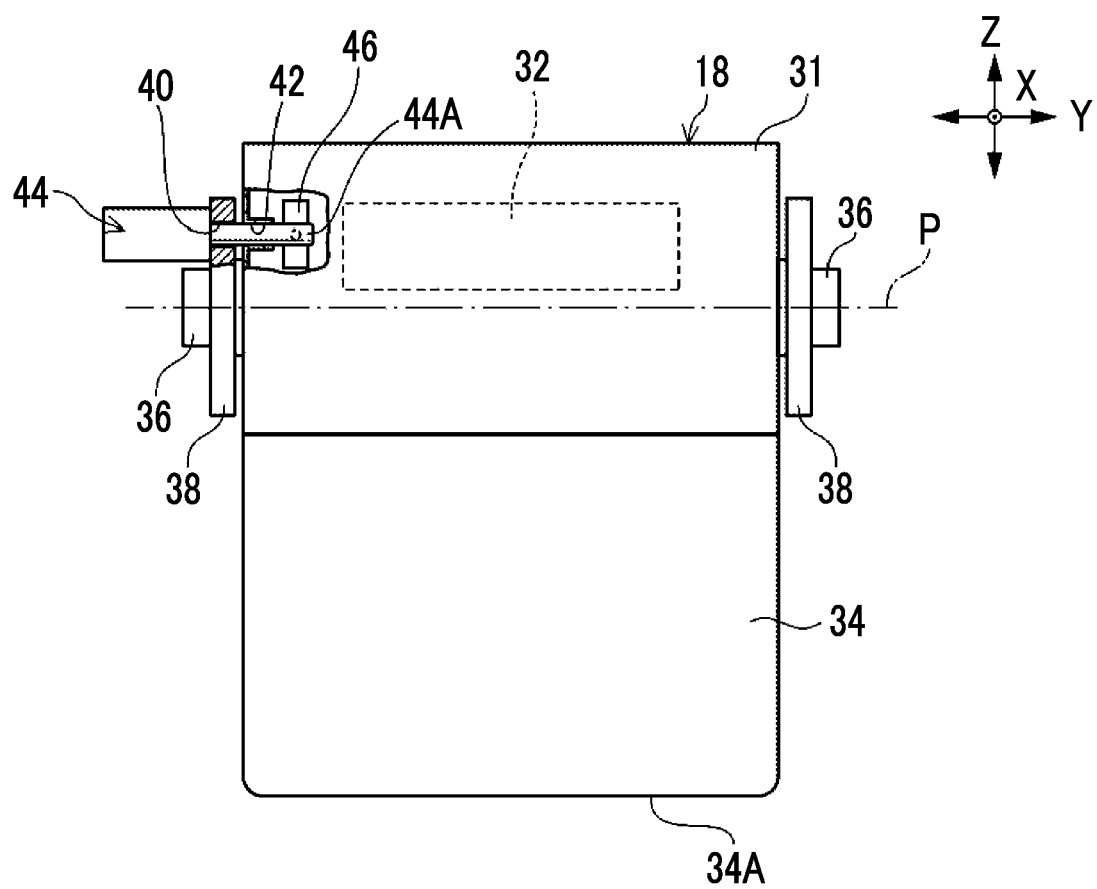
FIG. 4C is a front view illustrating a locked state of the irradiation unit illustrated in FIG. 4A.

The irradiation unit 18 can be rotated about an axis line P (see FIG. 4A) of a rotation shaft 36 that extends in the width direction of the radiography apparatus 10 (the Y direction in FIG. 1) as a rotation center with respect to the arm 12. Specifically, as illustrated in FIGS. 4A to 4C, a pair of attachment plates 38 are fixed to one end of the arm 12.

The pair of attachment plates 38 are disposed such that both sides of the irradiation unit 18 in the width direction are interposed therebetween and are connected to both side surfaces of the irradiation unit 18 in the width direction. The rotation shafts 36 are provided on each of the side surfaces of the irradiation unit 18 facing the attachment plates 38 so as to protrude. The rotation shafts 36 are supported by the pair of attachment plates 38 through bearings (not illustrated). Therefore, the irradiation unit 18 can be rotated about the axis line P of the rotation shaft 36 as the rotation center with respect to the attachment plates 38 and the orientation of the irradiation opening 34A of the irradiation unit 18 can be changed in the front-rear direction of the arm 12. The orientation of the irradiation opening 34A is changed to change the irradiation direction of radiation.

The irradiation unit 18 is connected to, for example, the control unit 28 and the power supply circuit (not illustrated) of the main body 16 illustrated in FIG. 1 by a cable (not illustrated) including a signal line for transmitting a control signal and a power line for supplying power.

Configuration of Image Receiving Unit

As illustrated in FIG. 1, the image receiving unit 20 is provided at the other end of the arm 12 which is a position facing the irradiation unit 18. The image receiving unit 20 comprises an image detector provided in a housing. The image receiving unit 20 has an image receiving surface 20A that receives the radiation which has been emitted from the irradiation unit 18 and then transmitted through the subject H. The radiation carrying the information of the subject H is incident on the image receiving surface 20A.

The image detector is, for example, a flat panel detector (FPD) of a digital radiography (DR) type. The FPD has a detection surface in which a plurality of pixels are two-dimensionally arranged and a thin film transistor (TFT) panel (not illustrated) for driving the pixels. Radiation is incident on the detection surface of the image detector through the image receiving surface 20A. The image detector converts the incident radiation into an electric signal and outputs a radiographic image indicating the subject H on the basis of the converted electric signal. For example, the image detector is an indirect conversion type that converts radiation into visible light using a scintillator and converts the converted visible light into an electric signal. In addition, the image detector may be a direct conversion type that directly converts radiation into an electric signal. Further, the image receiving unit 20 may have, for example, a configuration in which an image intensifier (I.I) and a camera are combined other than the configuration using the FPD.

Further, the image receiving unit 20 is connected to, for example, the control unit 28 and the power supply circuit (not illustrated) of the main body 16 by a cable (not illustrated) including a signal line for transmitting a control signal and a power line for supplying power.

Configuration of Locking Mechanism

As illustrated in FIGS. 4B and 4C, a through hole 40 that penetrates the attachment plate 38 in a thickness direction is formed in one of the pair of attachment plates 38 that rotatably support the irradiation unit 18. A through hole 42 having substantially the same diameter as the through hole 40 is formed in a side surface of the irradiation unit 18 which faces the one attachment plate 38.

Here, the through hole 42 of the irradiation unit 18 is formed at a position communicating with the through hole 40 of the attachment plate 38 in a case in which the irradiation unit 18 is in a facing posture in which the irradiation opening 34A and the image receiving surface 20A of the image receiving unit 20 (see FIG. 1) face each other.

Figure 5:
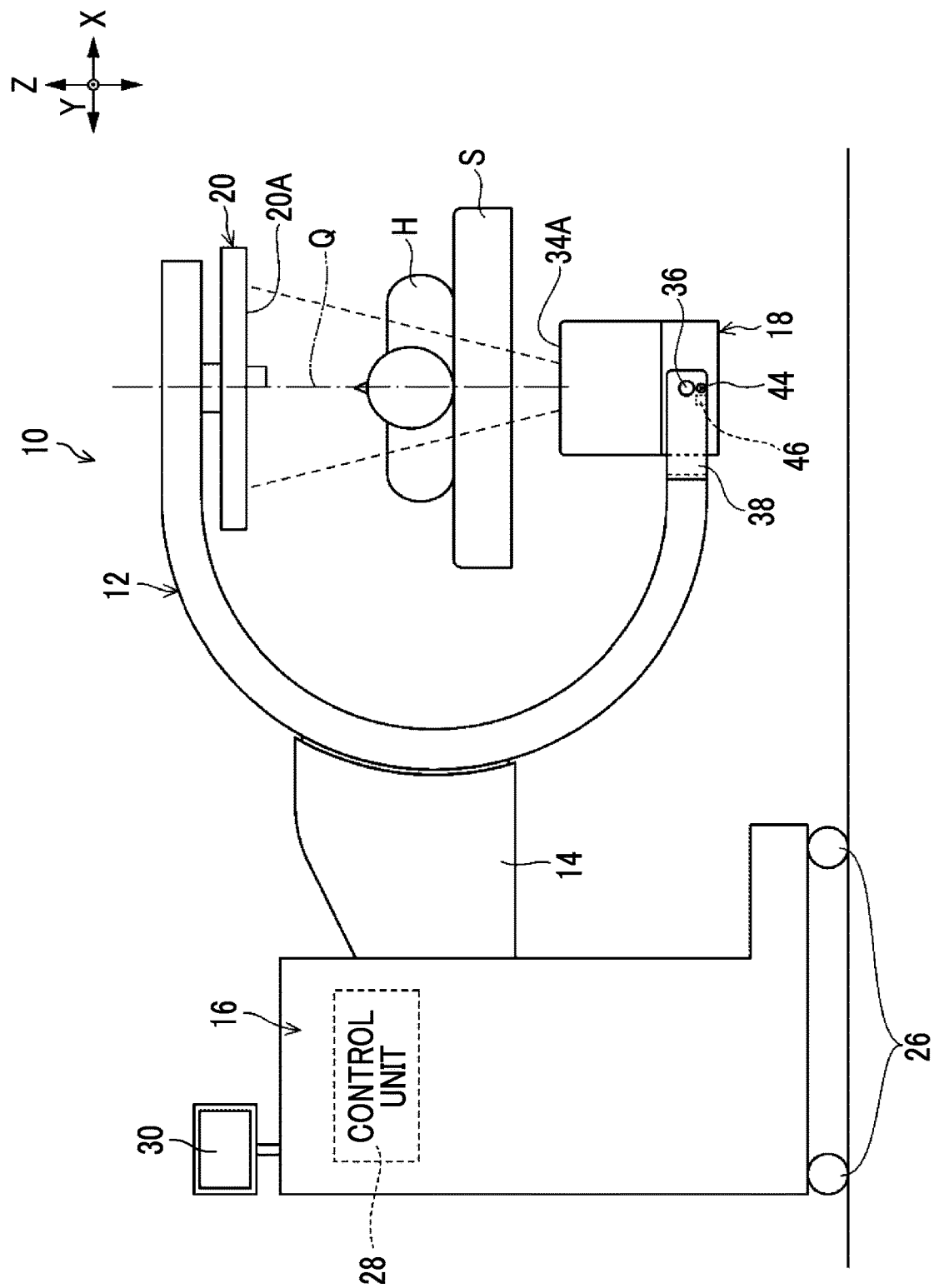
FIG. 5 is an overall side view illustrating an aspect of the use of the radiography apparatus according to the first embodiment.

In this embodiment, the "facing posture" means a confronting posture in which a central axis Q of a beam of radiation that spreads in a cone shape from the focus of the irradiation unit 18 through the irradiation opening 34A is aligned with a normal line Q to the image receiving surface 20A as illustrated in FIG. 5. The focus of the irradiation unit 18 is specifically the focus of the radiation tube 32.

Further, as illustrated in FIGS. 4A to 4C, a solenoid 44 as an example of a locking mechanism that locks the rotation of the irradiation unit 18 with respect to the arm 12 is attached to the attachment plate 38 in which the through hole 40 is formed. The solenoid 44 comprises a movable iron core 44A that is inserted into the through hole 40 of the attachment plate 38. The movable iron core 44A can be expanded and contracted by switching the energized state and the non-energized state of the solenoid 44.

Specifically, in a case in which the solenoid 44 is energized, the movable iron core 44A is attracted to the solenoid 44 and a leading end of the movable iron core 44A is located in the through hole 40 of the attachment plate 38 as illustrated in FIG. 4B. In this state, since the movable iron core 44A is not inserted into the through hole 42 of the irradiation unit 18, the irradiation unit 18 is in an unlocked state in which the irradiation unit 18 can be rotated with respect to the attachment plate 38, that is, the arm 12.

In contrast, in a state in which the through hole 40 of the attachment plate 38 and the through hole 42 of the irradiation unit 18 communicate with each other, that is, in a state in which the irradiation opening 34A is in the facing posture, the movable iron core 44A can be inserted into the through hole 42 of the irradiation unit 18 as illustrated in FIG. 4C. Therefore, in a case in which the solenoid 44 is de-energized in the state in which the irradiation opening 34A is in the facing posture, the leading end of the movable iron core 44A is inserted into the through hole 42 and reaches the inside of the irradiation unit 18 as illustrated in FIG. 4C. In this state, since the movable iron core 44A of the solenoid 44 is also inserted in the through hole 42 of the irradiation unit 18, the irradiation unit 18 is in a locked state in which the rotation of the irradiation unit 18 with respect to the attachment plate 38, that is, the arm 12 is restricted.

A photo sensor 46 is provided outside the through hole 42 in the irradiation unit 18. The photo sensor 46 is, for example, a reflective sensor in which a light emitting window through which a light emitting element (not illustrated) emits light and a light receiving window through which a light receiving element receives light are arranged on the same surface. For example, in the photo sensor 46, in a state in which the movable iron core 44A is located in front of the light emitting window and the light receiving window, the light emitted from the light emitting window is reflected by the movable iron core 44A. As a result, the amount of light received through the light receiving window increases. In contrast, in a state in which the movable iron core 44A is retracted from the front surfaces of the light emitting window and the light receiving window, light is not reflected by the movable iron core 44A. As a result, the amount of light received through the light receiving window is reduced. As such, the photo sensor 46 detects a change in the light which has been emitted from the light emitting window and then received by the light receiving element to detect whether or not the movable iron core 44A inserted into the through hole 42 of the irradiation unit 18 is present. The photo sensor 46 outputs an on signal as a detection signal to the control unit 28 while detecting that the movable iron core 44A is present and outputs an off signal as the detection signal to the control unit 28 while detecting that the movable iron core 44A is absent.

Configuration of Control Unit

Figure 6:
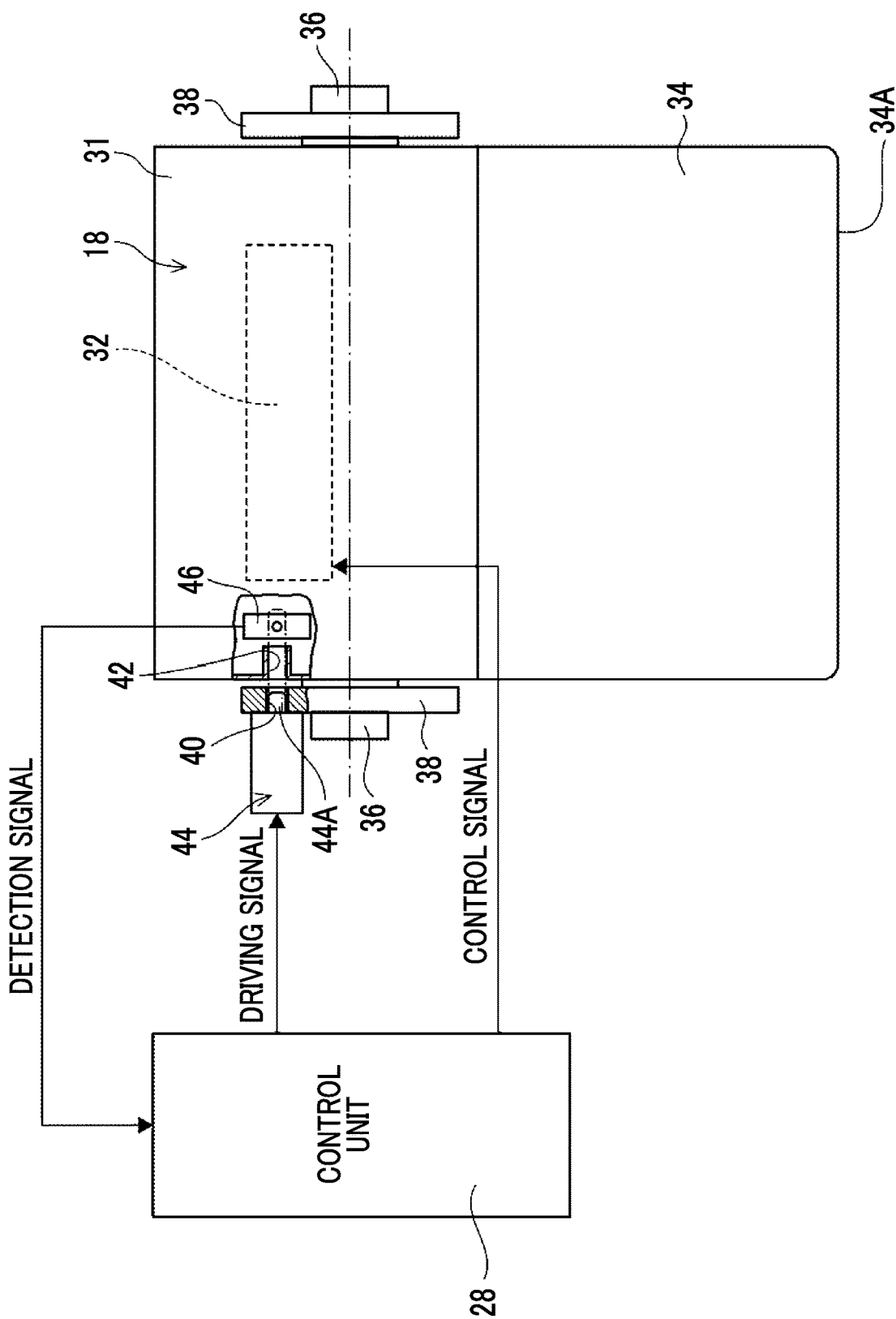
FIG. 6 is a block diagram illustrating a functional configuration of a control unit of the radiography apparatus according to the first embodiment.

As illustrated in FIG. 6, in the radiography apparatus 10, the control unit 28 provided in the main body 16 (see FIG. 1) transmits a control signal to the radiation tube 32 of the irradiation unit 18 to control, for example, the tube voltage, tube current, and irradiation time of radiation of the radiation tube 32. The tube voltage is controlled to control the energy of radiation and the tube current and the irradiation time are controlled to control the dose of radiation. In practice, since a high voltage is applied to the radiation tube 32, the control unit 28 controls the radiation tube 32 through a high-voltage generation device (not illustrated). In imaging, imaging conditions including, for example, the tube voltage, the tube current, and the irradiation time are set through the operation panel 30. The control unit 28 operates the irradiation unit 18 on the basis of the set imaging conditions.

The control unit 28 directs the irradiation unit 18 to perform moving image capture irradiation in which the irradiation unit 18 continuously emits radiation such that a moving image of the subject H (see FIG. 1) can be captured. Here, the term "continuous emission of radiation" includes not only continuous emission in which radiation is continuously emitted but also so-called pulse emission in which radiation is repeatedly emitted at a preset short time interval.

In a case in which a moving image is captured, the control unit 28 operates the image detector of the image receiving unit 20 in synchronization with the moving image capture irradiation by the irradiation unit 18. In a case in which a moving image is captured, basically, the irradiation time is not set as an imaging condition and commands to start and end the capture of the moving image are input through the operation panel 30. In a case in which the command to start the capture of a moving image is input, the control unit 28 directs the irradiation unit 18 to start the emission of radiation under preset imaging conditions. Of course, the commands to start and end the capture of a moving image may be input by, for example, a foot switch other than the operation panel 30.

In the capture of a moving image, the image detector repeats an image detection operation at a preset frame rate while the moving image capture irradiation is performed. An image output by the image detector is transmitted to the control unit 28. The control unit 28 sequentially outputs the received images to a monitor (not illustrated). Then, the moving image of the subject H is displayed on the monitor.

In addition, the control unit 28 directs the irradiation unit 18 to perform still image capture irradiation in which the irradiation unit 18 emits radiation for a shorter time than in the moving image capture irradiation such that a still image of the subject H (see FIG. 1) can be captured.

In the capture of a still image, the control unit 28 operates the image detector of the image receiving unit 20 in synchronization with the irradiation timing in the irradiation for capturing a still image by the irradiation unit 18. For example, a command to capture a still image is input through an irradiation switch (not illustrated) that is connected to the control unit 28. In the capture of a still image, the irradiation time is, for example, in the order of several tens of milliseconds to several hundreds of milliseconds. In a case in which a command to capture a still image is input, the control unit 28 operates the irradiation unit 18 on the basis of preset imaging conditions. In the capture of a still image, in a case in which the set irradiation time elapses, the irradiation operation of the irradiation unit 18 ends since the irradiation time is set in the imaging conditions.

In a case in which the irradiation ends, the image detector starts to output the detected image. The image output by the image detector is transmitted to the control unit 28. The control unit 28 stores data of the still image in a memory (not illustrated). Then, the stored still image is displayed on the monitor (not illustrated). Therefore, the still image of the subject H is displayed on the monitor. Further, the still image may be displayed on the operation panel 30 in order to check the captured still image immediately after the image is captured.

Further, the control unit 28 controls the solenoid 44. In a case in which an unlocking command is input through the operation panel 30 (see FIG. 1) in a state in which the rotation of the irradiation unit 18 with respect to the arm 12 is locked by the solenoid 44, the control unit 28 transmits a driving signal to the solenoid 44 to energize the solenoid 44. Then, the movable iron core 44A is attracted by the solenoid 44 and the irradiation unit 18 is unlocked.

In contrast, in a case in which a locking command is input through the operation panel 30 (see FIG. 1), the control unit 28 de-energizes the supply of power to the solenoid 44. In this case, since the through hole 40 of the attachment plate 38 and the through hole 42 of the irradiation unit 18 communicate with each other in a state in which the irradiation opening 34A is in the facing posture, the movable iron core 44A is also inserted into the through hole 42 of the irradiation unit 18 to lock the irradiation unit 18.

In a case in which the irradiation opening 34A is not in the facing posture, that is, in a case in which the through hole 40 of the attachment plate 38 and the through hole 42 of the irradiation unit 18 do not communicate with each other, it is difficult to insert the movable iron core 44A into the through hole 42 even though the locking command is input. Therefore, the irradiation unit 18 is not locked. As such, the control unit 28 controls the energization of the solenoid 44 to switch the irradiation unit 18 between the locked state and the unlocked state.

Further, the control unit 28 determines whether or not the rotation of the irradiation unit 18 is locked on the basis of a detection signal from the photo sensor 46 provided in the irradiation unit 18. In a case in which the movable iron core 44A is in the through hole 42 of the irradiation unit 18, the control unit 28 receives an on signal as the detection signal from the photo sensor 46. The control unit 28 determines that the rotation of the irradiation unit 18 is locked while receiving the on signal from the photo sensor 46. On the other hand, in a case in which the movable iron core 44A is not in the through hole 42 of the irradiation unit 18, the control unit 28 receives an off signal as the detection signal from the photo sensor 46. The control unit 28 determines that the rotation of the irradiation unit 18 is not locked while receiving the off signal from the photo sensor 46.

Method for Controlling Radiography Apparatus

Figure 7:
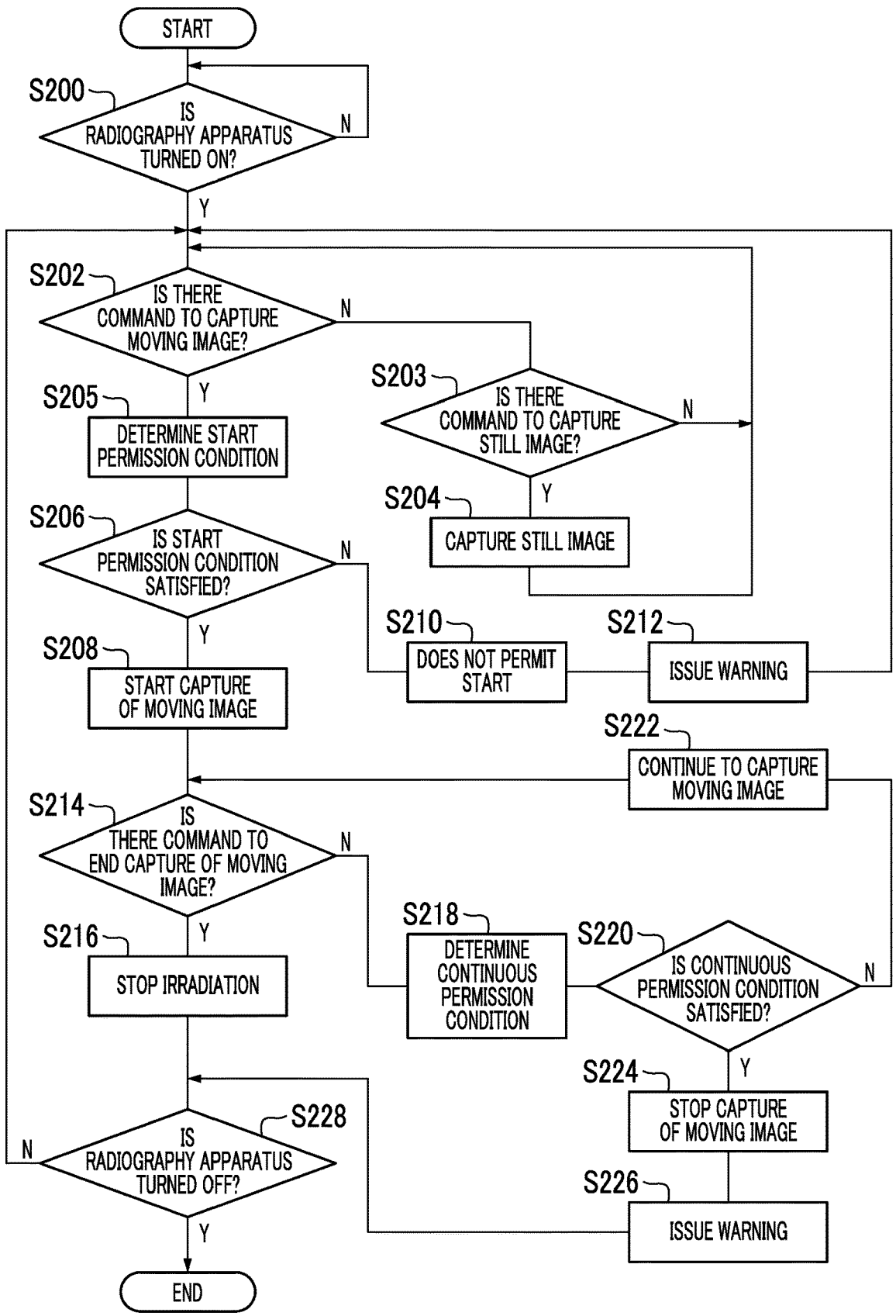
FIG. 7 is a flowchart illustrating a processing procedure of the control unit of the radiography apparatus according to the first embodiment.

Next, a method for controlling the radiography apparatus 10 according to this embodiment will be described with reference to a flowchart illustrated in FIG. 7.

First, in Step S200, in a case in which the radiography apparatus 10 is turned on by the operation of a power switch (not illustrated) (Y in Step S200), the control unit 28 starts to control the radiography apparatus 10. In a case in which the control by the control unit 28 is started, it is possible to receive the input of the imaging conditions through the operation panel 30. The control unit 28 waits for a command to capture a moving image or a still image.

In Step S202, the control unit 28 waits for a command to capture a moving image from the operator. In a case in which there is no command to capture a moving image (N in Step S202), the process proceeds to Step S203 and waits for a command to capture a still image. In a case in which there is no command to capture a still image in Step S203 (N in Step S203), the process returns to Step S202. In a case in which there is a command to capture a still image in Step S203, the control unit 28 performs the capture of a still image (Step S204). In a case in which the capture of the still image ends, the process returns to Step S202.

In Step S202, in a case in which a command to capture a moving image is input through the operation panel 30 (Y in Step S202), the process proceeds to Step S205.

In Step S205, first, the control unit 28 performs a start permission condition determination process for the capture of a moving image. In the start permission condition determination process, the control unit 28 determines whether or not a start permission condition is satisfied (Step S206). Here, in this embodiment, the "start permission condition" for the capture of a moving image is that the rotation of the irradiation unit 18 with respect to the arm 12 is locked by the solenoid 44.

In a case in which it is determined that the start permission condition is satisfied, that is, the rotation of the irradiation unit 18 with respect to the arm 12 is locked by the solenoid 44 (Y in Step S206), the control unit 28 transmits a control signal to the radiation tube 32 to start the capture of a moving image (Step S208).

On the other hand, in a case in which it is determined that the start permission condition for the capture of a moving image is not satisfied, that is, the rotation of the irradiation unit 18 with respect to the arm 12 is not locked by the solenoid 44 (N in Step S206), the control unit 28 does not permit the capture of a moving image (Step S210) and issues a warning (Step S212). Then, the process returns to Step S202.

The warning is issued, for example, by displaying a warning message indicating that it is difficult to start the capture of a moving image on the operation panel 30 as a warning unit. In addition, the warning may be issued, for example, by outputting a warning sound through a speaker (not illustrated) or by turning on a lamp (not illustrated).

After starting the capture of a moving image in Step S208, the control unit 28 determines whether or not a command to end the capture of a moving image has been input from the operator through the operation panel 30 (Step S214). Then, in a case in which the command has been input, the control unit 28 transmits a control signal to the radiation tube 32 of the irradiation unit 18 to stop the emission of radiation (Step S216). Then, the process proceeds to Step S228.

In Step S214, in a case in which the command to end the capture of a moving image has not been input, the control unit 28 performs a continuation permission condition determination process for the capture of a moving image (Step S218). In the continuation permission condition determination process, the control unit 28 determines whether or not a continuation permission condition is satisfied (Step S220). In this embodiment, similarly to the "start permission condition", the "continuation permission condition" is that the rotation of the irradiation unit 18 with respect to the arm 12 is locked by the solenoid 44.

In a case in which it is determined that the continuation permission condition is satisfied, that is, the rotation of the irradiation unit 18 with respect to the arm 12 is locked by the solenoid 44 (Y in Step S220), the capture of a moving image is continued (Step S222). Then, the process returns to Step S214.

On the other hand, in a case in which it is determined that the continuation permission condition is not satisfied, that is, the rotation of the irradiation unit 18 with respect to the arm 12 is not locked by the solenoid 44 (N in Step S220), the capture of a moving image is stopped (Step S224) and a warning is issued (Step S226). Then, the process proceeds to Step S228. For example, the warning is issued by displaying a warning message indicating that it is difficult to start the capture of a moving image on the operation panel 30 as the warning unit, similarly to the warning in Step S212.

In Step S228, the control unit 28 determines whether or not the radiography apparatus 10 has been turned off by the operation of a power switch (not illustrated) by the operator. Then, in a case in which the radiography apparatus 10 has not been turned off (N in Step S228), the process returns to Step S202. On the other hand, in a case in which the radiography apparatus 10 has been turned off (Y in Step S228), the control unit 28 ends the control of the radiography apparatus 10.

As illustrated in Steps 203 and 204, in the capture of a still image, unlike the capture of a moving image, in a case in which the operator inputs a command to capture a still image, the control unit 28 performs the capture of a still image unless a moving image is captured. That is, the control unit 28 permits the capture of a still image, without performing the start permission condition determination process and the continuation permission condition determination process for the capture of a moving image, unlike the capture of a moving image. This corresponds to that the control unit 28 permits the still image capture irradiation by the irradiation unit 18 even in a case in which the moving image capture irradiation by the irradiation unit 18 is prohibited.

Operation and Effect

In a case in which radiation is emitted from the irradiation unit 18 in a state in which the irradiation opening 34A of the irradiation unit 18 and the image receiving surface 20A of the image receiving unit 20 do not face each other, there is a concern that the irradiation field of the radiation will deviate from the image receiving surface 20A. In particular, in the capture of a moving image, radiation is continuously emitted for a relatively long time. Therefore, in a case in which the irradiation field of radiation deviates from the image receiving surface 20A, unnecessary radiation that does not contribute to the capture of a moving image is continuously emitted.

Here, the radiography apparatus 10 according to this embodiment comprises the solenoid 44 that locks the rotation of the irradiation unit 18 with respect to the arm 12 in the facing posture in which the irradiation opening 34A faces the image receiving surface 20A of the image receiving unit 20.

Then, in a state in which the rotation of the irradiation unit 18 with respect to the arm 12 is locked by the solenoid 44, the control unit 28 performs control (corresponding to first control) to perform the moving image capture irradiation. Therefore, a moving image can be captured in the facing posture in which the irradiation opening 34A of the irradiation unit 18 faces the image receiving surface 20A of the image receiving unit 20.

In contrast, in a case in which the rotation of the irradiation unit 18 is not locked by the solenoid 44, the irradiation opening 34A is likely to deviate from the facing posture. Here, according to the radiography apparatus 10 of this embodiment, the control unit 28 performs control (corresponding to the first control) to prohibit the moving image capture irradiation in a state in which the irradiation unit 18 is unlocked. Therefore, it is possible to suppress the emission of radiation in a state in which the irradiation field of the radiation deviates from the image receiving surface 20A. Therefore, it is possible to suppress the emission of unnecessary radiation that does not contribute to the capture of a moving image. The suppression of the emission of unnecessary radiation makes it possible to suppress unnecessary exposure to medical staff such as the operator of the radiography apparatus 10.

For example, the amount of projection of the irradiation field of radiation from the image receiving surface 20A is defined by the JIS standard (JIS-Z-4751-2-54: 2017). In this embodiment, it is possible to suppress the emission of radiation in a state in which the irradiation field of the radiation deviates from the image receiving surface 20A. Therefore, it is easy to conform to this standard.

The control to prohibit the moving image capture irradiation by the control unit 28 includes control to prohibit the start of the moving image capture irradiation in a case in which there is a command to start the capture of a moving image and control to stop the moving image capture irradiation while a moving image is being captured. As such, it is possible to suppress the emission of unnecessary radiation that does not contribute to the capture of a moving image by prohibiting the start of the moving image capture irradiation in a state in which the capture of a moving image is not started and by stopping the moving image capture irradiation while a moving image is being captured.

In particular, according to this embodiment, the solenoid 44 locks the rotation of the irradiation unit 18 with respect to the arm 12 in the confronting posture in which the central axis Q of the radiation beam that spreads in a cone shape from the focus of the irradiation unit 18 through the irradiation opening 34A is aligned with the normal line Q to the image receiving surface 20A. The moving image capture irradiation is prohibited in postures other than the confronting posture by the above-mentioned configuration. Therefore, it is possible to further suppress the emission of unnecessary radiation that does not contribute to the capture of a moving image.

Further, according to this embodiment, the irradiation unit 18 is rotatable with respect to the arm 12 such that the orientation of the irradiation opening 34A is changed in the front-rear direction of the arm 12. As such, the orientation of the irradiation opening 34A of the irradiation unit 18 is rotated with respect to the arm 12 in the front-rear direction of the arm 12 to adjust the orientation of the irradiation opening 34A without moving the arm 12. It is more convenient to adjust the orientation of the irradiation opening 34A according to an imaging part of the subject H in the capture of a still image. On the other hand, in a case in which the irradiation opening 34A and the image receiving surface 20A do not face each other, it is necessary to prohibit the capture of a moving image in order to suppress the emission of unnecessary radiation as described above. According to this embodiment, it is possible to meet the demands for both the convenience of the capture of a still image and the suppression of the emission of unnecessary radiation in the capture of a moving image. As described above, the technology of the present disclosure is particularly effective in a case in which a mechanism for adjusting the orientation of the irradiation opening 34A is provided in consideration of the convenience of the capture of a still image.

Further, according to this embodiment, a warning is issued by the operation panel 30 as the warning unit in a case in which the control unit 28 prohibits the start of the moving image capture irradiation and in a case in which the moving image capture irradiation is stopped while a moving image is being captured. Therefore, it is possible to notify the operator that the capture of a moving image is prohibited or that the capture of a moving image is stopped.

Furthermore, the radiography apparatus 10 according to this embodiment can direct the irradiation unit 18 to perform still image capture irradiation in addition to the moving image capture irradiation. Unlike the capture of a moving image, in many cases, the irradiation direction of the irradiation unit 18 is changed to various directions and then the irradiation unit 18 is used in the capture of a still image. Here, according to this embodiment, even in a case in which the moving image capture irradiation is prohibited, the control unit 28 permits the still image capture irradiation. Therefore, it is possible to change the irradiation direction of the irradiation unit 18 to various directions and then to capture a still image. As a result, it is possible to improve convenience.

In the above-described example, an example of the facing posture is the confronting posture in which the central axis Q (see FIG. 5) of the radiation beam is aligned with the normal line to the image receiving surface 20A. However, the confronting posture includes, for example, a case in which the central axis Q and the normal line to the image receiving surface 20A deviate from each other within a tolerance range due to an assembly error during manufacture, individual differences, and the like. The facing posture includes not only the confronting posture but also a case in which the deviation between the central axis Q and the normal line to the image receiving surface 20A is out of the tolerance range as long as the irradiation field of radiation by the irradiation unit 18 is within a range included in the image receiving surface 20A. Of course, it is most preferable to permit the capture of a moving image only in the confronting posture and to prohibit the capture of a moving image in the other postures from the viewpoint of suppressing unnecessary irradiation.

Second Embodiment

Next, a radiography apparatus according to a second embodiment of the present disclosure will be described with reference to FIGS. 8 to 10. In addition, the same configurations as those in the first embodiment are denoted by the same reference numerals and the description thereof will not be repeated. The description is focused on the differences between the first and second embodiments.

The radiography apparatus 10 according to the first embodiment includes the solenoid 44 as the locking mechanism that locks the rotation of the irradiation unit 18 and the photo sensor 46 that detects the locked state. Instead of this configuration, a radiography apparatus 50 according to this embodiment includes a posture detection unit 62 that detects whether or not an irradiation opening 58A of an irradiation unit 58 is in a facing posture in which it faces an image receiving surface 60A of an image receiving unit 60 as illustrated in FIG. 9A.

Figure 8A:
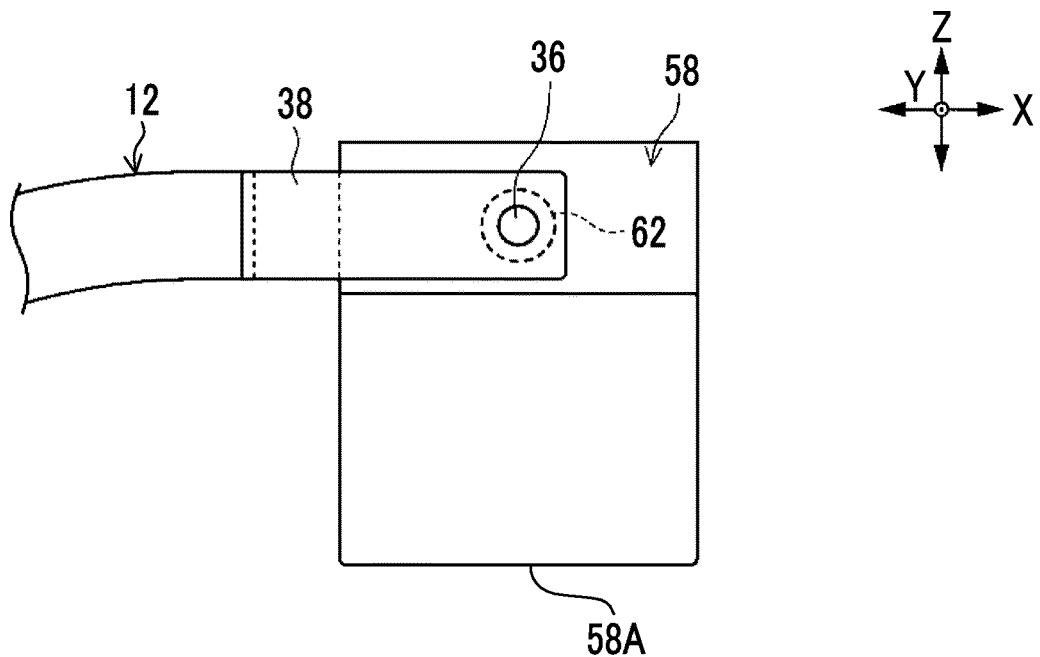
FIG. 8A is a partial side view illustrating an irradiation unit of a radiography apparatus according to a second embodiment.
Figure 8B:
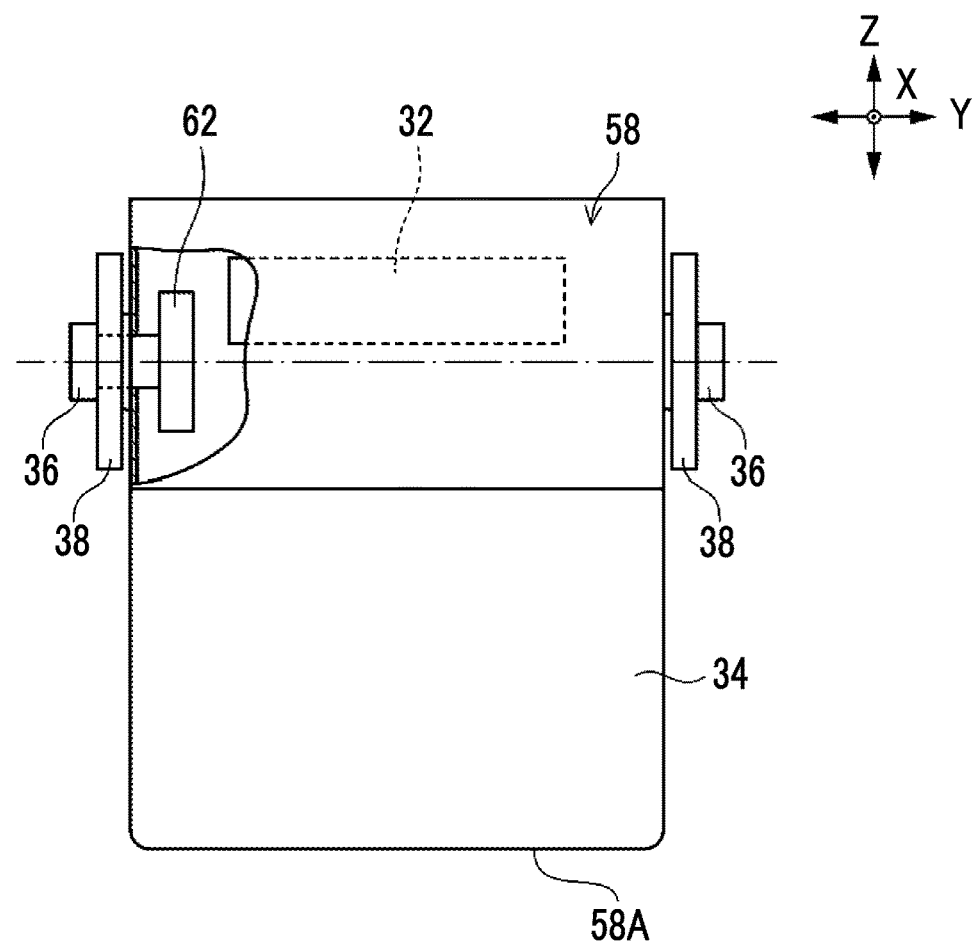
FIG. 8B is a front view illustrating the irradiation unit illustrated in FIG. 8A.

As illustrated in FIGS. 8A and 8B, the posture detection unit 62 is, for example, a rotary potentiometer that is attached to a rotation shaft 36 of the irradiation unit 58. The posture detection unit 62 includes a resistor (not illustrated) and a slider (not illustrated) that slides on the surface of the resistor as the rotation shaft 36 rotates and the resistance value of the posture detection unit 62 change on the basis of the rotation angle of the rotation shaft 36. Therefore, the posture detection unit 62 can detect the resistance value to detect the rotation angle of the rotation shaft 36 with respect to the attachment plate 38.

Figure 9A:
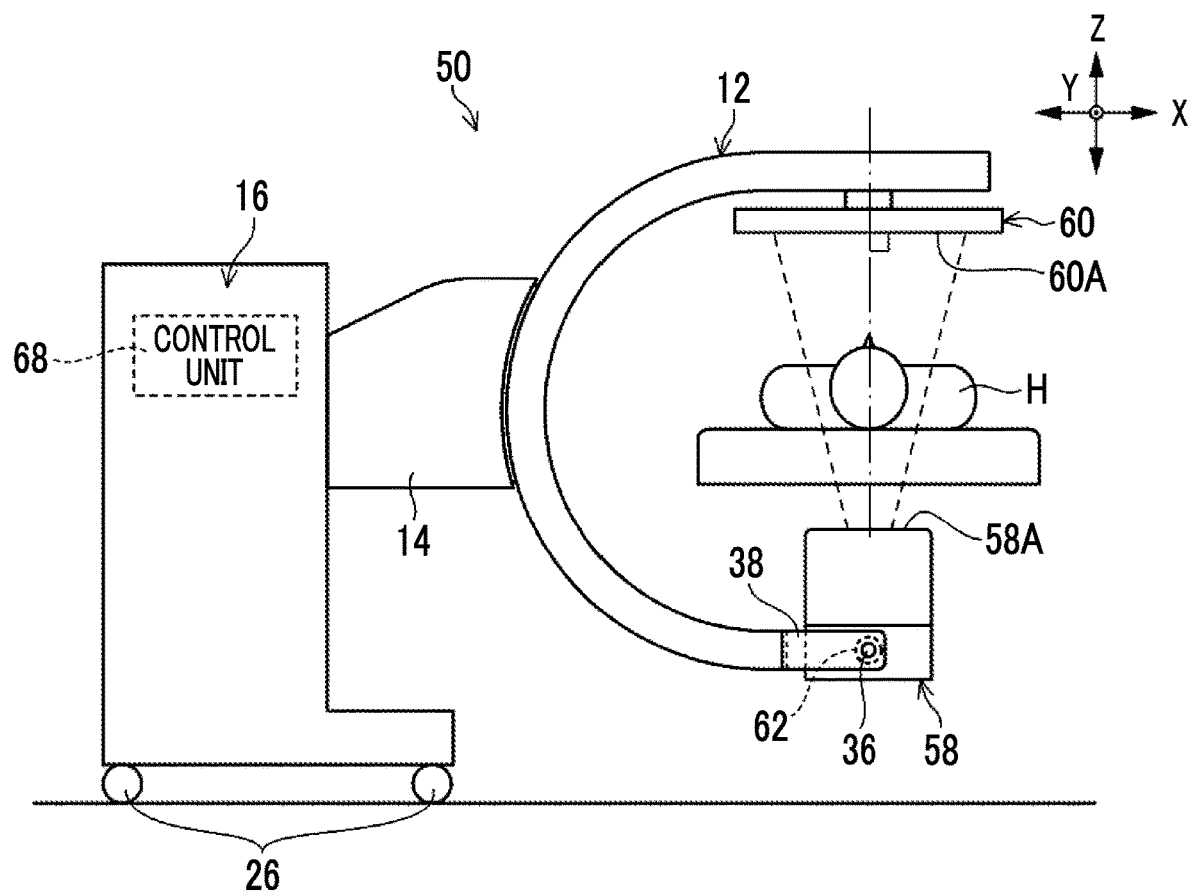
FIG. 9A is an overall side view illustrating an aspect of the use of the radiography apparatus according to the second embodiment.

For example, it is assumed that the rotation angle of the rotation shaft 36 with respect to the attachment plate 38 (arm 12) is a reference angle in a case in which the irradiation opening 58A is in a facing posture (confronting posture) in which it faces the image receiving surface 60A, as illustrated in FIG. 9A. In this case, the posture detection unit 62 detects the rotation angle of the rotation shaft 36 with respect to the reference angle to detect whether or not the irradiation opening 58A is in the facing posture.

As illustrated in FIG. 10, a detection signal from the posture detection unit 62 is transmitted to a control unit 68 that is provided in the main body (see FIG. 9A). For example, as illustrated in FIG. 9A, in a posture in which the irradiation opening 58A of the irradiation unit 58 faces the image receiving surface 60A of the image receiving unit 60, the posture detection unit 62 detects that the rotation shaft 36 is at the reference angle. In this case, the posture detection unit 62 outputs a signal corresponding to the reference angle as the detection signal to the control unit 68 in a case in which the rotation shaft 36 is at the reference angle, that is, in a state in which the irradiation opening 58A is in the facing posture with respect to the image receiving surface 60A. The control unit 68 determines that the irradiation opening 58A is in the facing posture while receiving the detection signal corresponding to the reference angle.

Figure 9B:
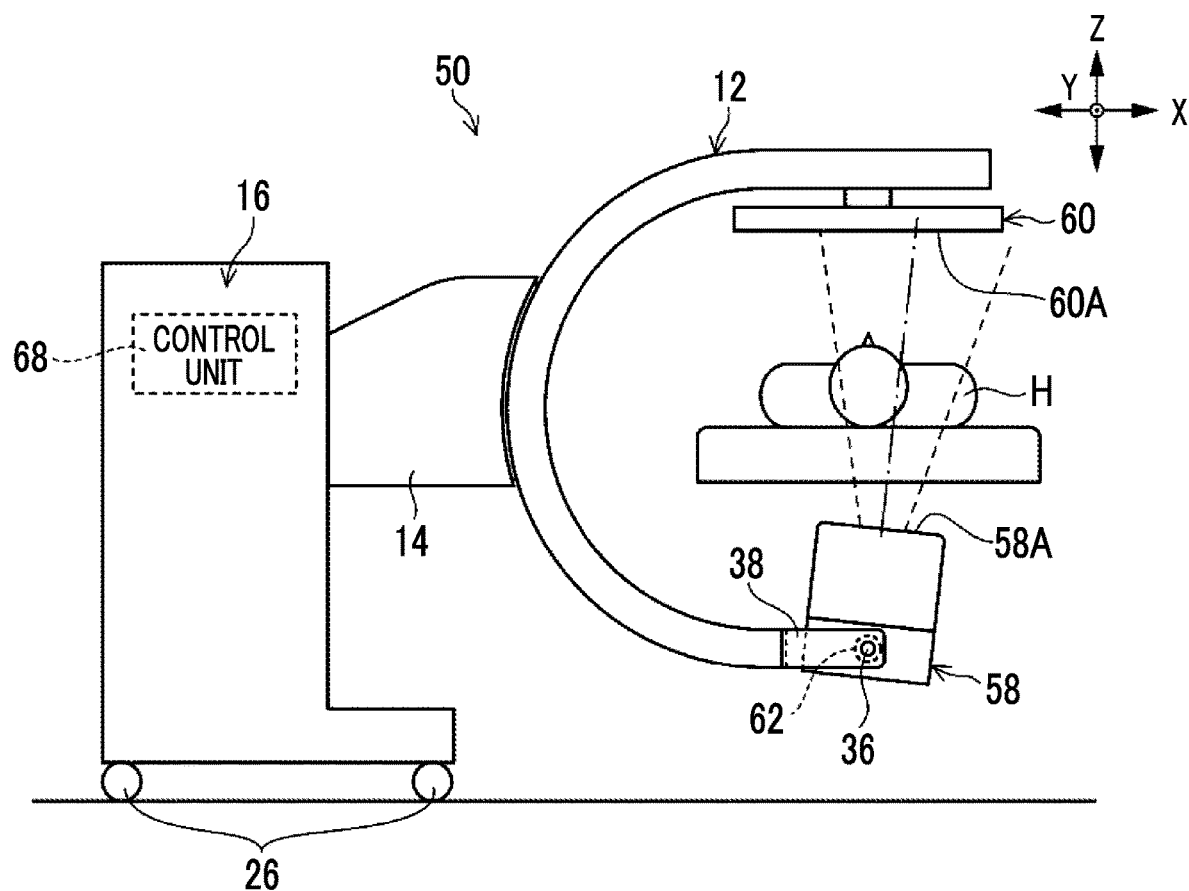
FIG. 9B is an overall side view illustrating a comparative example of the radiography apparatus illustrated in FIG. 9A.

In contrast, the posture detection unit 62 detects that the rotation shaft 36 is not at the reference angle in a posture in which the irradiation opening 58A of the irradiation unit 58 does not face the image receiving surface 60A of the image receiving unit 60 as illustrated in FIG. 9B. In this case, the posture detection unit 62 outputs a signal corresponding to an angle other than the reference angle as the detection signal to the control unit 68 in a case in which the rotation shaft 36 is not at the reference angle, that is, in a state in which the irradiation opening 58A is not in the facing posture with respect to the image receiving surface 60A. The control unit 68 determines that the irradiation opening 58A is not in the facing posture while receiving a detection signal corresponding to an angle other than the reference angle.

The control flow procedure of the control unit 68 according to this embodiment is the same as the control flow procedure of the control unit 28 according to the first embodiment. Here, in the control flow according to the first embodiment, the "start permission condition" for the capture of a moving image in Step S205 and the "continuation permission condition" for the capture of a moving image in Step S218 are that the rotation of the irradiation unit 18 with respect to the arm 12 is locked by the solenoid 44.

In contrast, in this embodiment, the "start permission condition" and the "continuation permission condition" are that the posture detection unit 62 detects that the irradiation opening 58A is in the facing posture. In a case in which the control unit 68 determines that the irradiation opening 58A is in the facing posture, it permits (or continues) the moving image capture irradiation. In a case in which the control unit 68 determines that the irradiation opening 58A is not in the facing posture, it prohibits (or stops) the moving image capture irradiation.

Operation and Effect

The radiography apparatus 50 according to this embodiment comprises the posture detection unit 62 that detects the rotation angle of the rotation shaft 36 of the irradiation unit 58 to detect whether or not the irradiation opening 58A is in the facing posture.

Then, the control unit 68 performs control (corresponding to second control) to permit the moving image capture irradiation in a state in which the posture detection unit 62 detects that the irradiation opening 58A is in the facing posture, that is, in a state in which the rotation angle of the rotation shaft 36 is the reference angle. Therefore, it is possible to capture a moving image in a posture in which the irradiation opening 58A of the irradiation unit 58 surely faces the image receiving surface 60A of the image receiving unit 60.

In contrast, the control unit 68 performs control (corresponding to the second control) to prohibit the moving image capture irradiation in a state in which the posture detection unit 62 does not detect that the irradiation opening 58A is in the facing posture, that is, in a state in which the rotation angle of the rotation shaft 36 is not the reference angle. Therefore, it is possible to suppress the emission of radiation in a state in which the irradiation field of the radiation deviates from the image receiving surface 60A and to suppress the emission of unnecessary radiation that does not contribute to the capture of a moving image.

Third Embodiment

Next, a radiography apparatus according to a third embodiment of the present disclosure will be described with reference to FIGS. 11 to 15. In addition, the description and illustration of the same configurations as those in the first embodiment will be omitted and the description is focused on the differences between the first and third embodiments.

In the radiography apparatus 10 according to the first embodiment, the image receiving unit 20 is fixed to the other end of the arm 12. In contrast, in a radiography apparatus 70 according to this embodiment, an image receiving unit 80 is attachable to and detachable from the arm 12 as illustrated in FIG. 14.

Specifically, as illustrated in FIG. 11, an accommodation portion 82 for accommodating the image receiving unit 80 is provided at the other end of the arm 12. The accommodation portion 82 is a box with a flat rectangular parallelepiped shape and an opening 82A for accommodating the image receiving unit 80 in the accommodation portion 82 is formed in one of four side surfaces. Further, an opening 82B with a square shape is also formed in the upper surface of the accommodation portion 82 which faces the irradiation opening 34A (see FIG. 14) of the irradiation unit 18.

The image receiving unit 80 is configured by providing an image detector, such as a flat panel detector, in a housing as in the first embodiment. In addition, in this embodiment, the image receiving unit 80 is a portable type that is attachably and detachably accommodated in the accommodation portion 82. The portable image receiving unit 80 is called, for example, an electronic cassette.

The portable image receiving unit 80 has, for example, a battery and a wireless communication unit which are not illustrated and can wirelessly communicate with a control unit 88 (see FIG. 14) provided in the main body 16. In a case in which a wireless communication unit is used, the image receiving unit 80 is driven by power from the battery and can be used in a so-called cableless manner. Therefore, as illustrated in FIG. 14, the image receiving unit 80 can be used in a state in which it is detached from the accommodation portion 82 (arm 12).

Figure 12A:
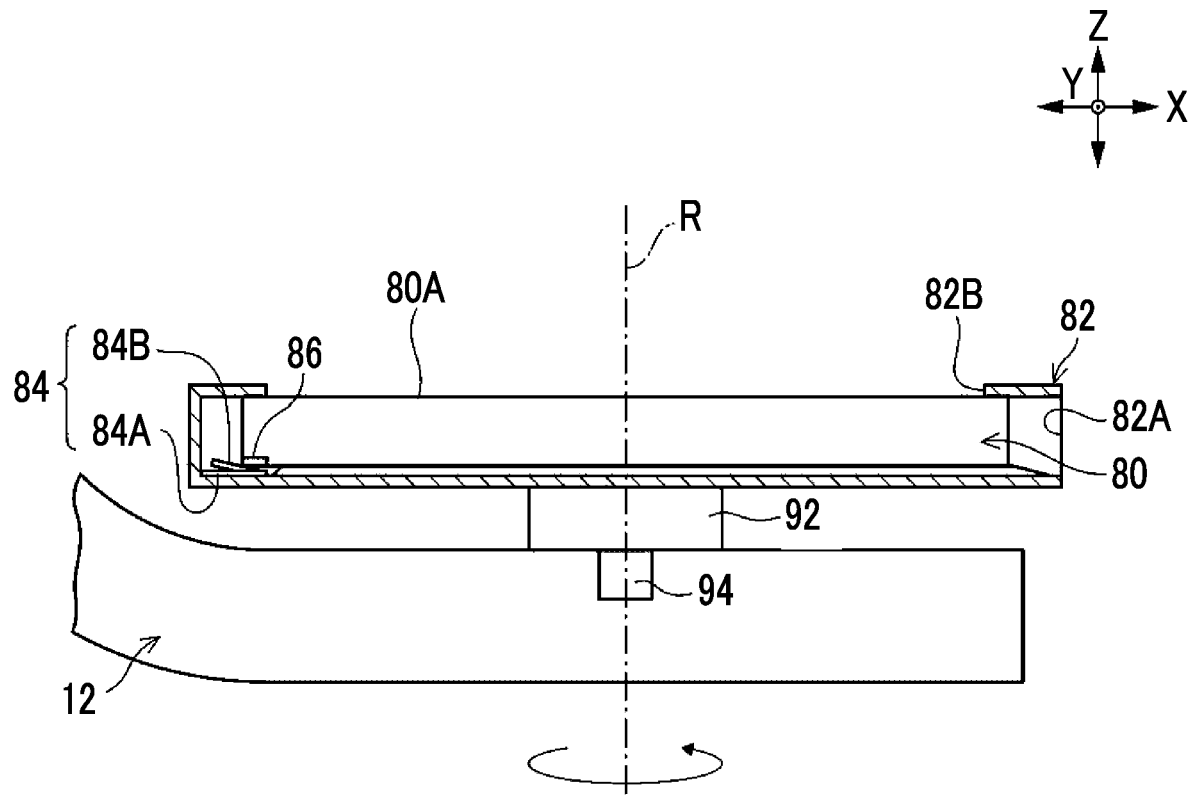
FIG. 12A is a cross-sectional view illustrating an example of the image receiving unit of the radiography apparatus according to the third embodiment.

In contrast, in a state in which the image receiving unit 80 is attached to the accommodation portion 82, an image receiving surface 80A of the image receiving unit 80 is exposed through the opening 82B formed in the upper surface of the accommodation portion 82 as illustrated in FIG. 12A. Therefore, even in a state in which the image receiving unit 80 is attached to the accommodation portion 82, the radiation emitted from the irradiation unit 18 (see FIG. 14) can be received by the image receiving surface 80A of the image receiving unit 80.

Further, the accommodation portion 82 comprises a contact sensor 84 as an example of an attachment and detachment detection unit that detects whether or not the image receiving unit 80 is detached from the accommodation portion 82. In this embodiment, the contact sensor 84 includes a terminal substrate 84A and a metal terminal 84B that is provided upright on the terminal substrate 84A. The terminal substrate 84A and the metal terminal 84B are provided on a side surface which is opposite to the side surface in which the opening 82A is formed in the accommodation portion 82.

A contact point 86 with the metal terminal 84B is provided at the lower end of the image receiving unit 80. In a case in which the image receiving unit 80 is accommodated in the accommodation portion 82 through the opening 82A, the contact point 86 of the image receiving unit 80 comes into contact with the metal terminal 84B of the accommodation portion 82. A change in capacitance at this time is detected as an electric signal to detect whether or not the image receiving unit 80 is accommodated in the accommodation portion 82, that is, whether or not the image receiving unit 80 is attached to the arm 12.

The attachment and detachment detection unit is not limited to the contact sensor 84 as long as it has a function of detecting whether or not the image receiving unit 80 is detached from the accommodation portion 82. For example, as illustrated in FIG. 12B, a non-contact sensor 90 may be used as the attachment and detachment detection unit.

Figure 12B:
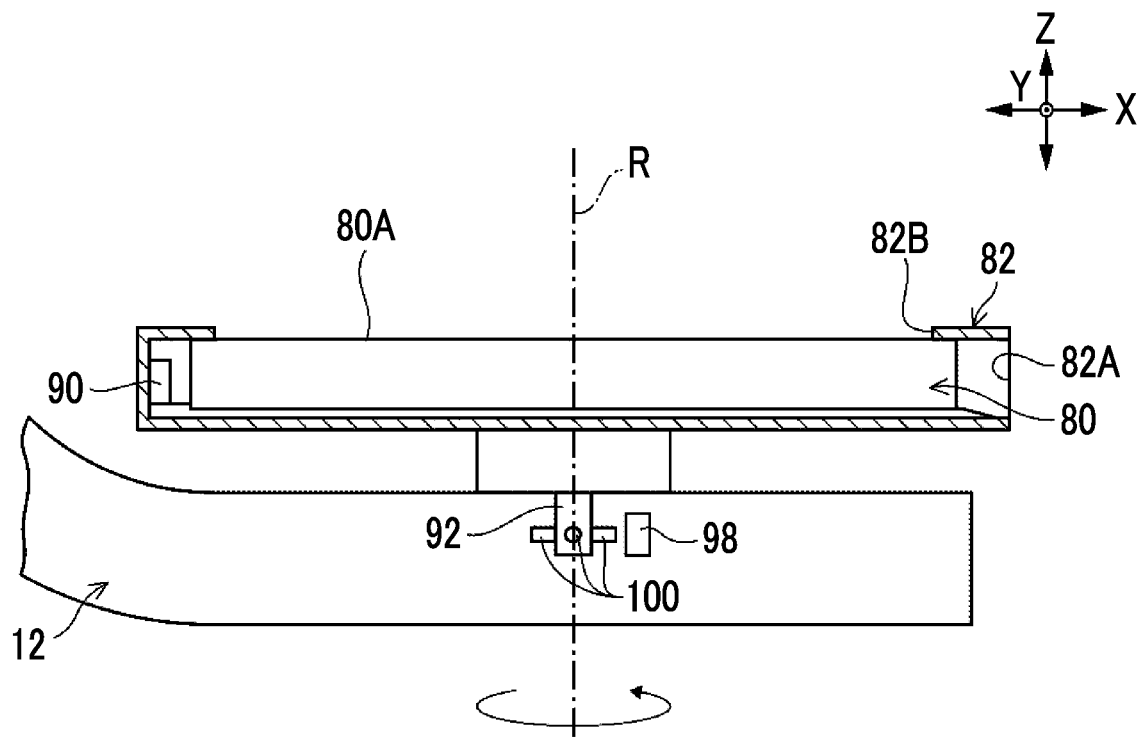
FIG. 12B is a cross-sectional view illustrating a modification example of the image receiving unit of the radiography apparatus according to the third embodiment.

The non-contact sensor 90 illustrated in FIG. 12B is the same as, for example, the photo sensor 46 according to the first embodiment. The non-contact sensor 90 can detect a change in the amount of light which has been emitted from a light emitting element and then received by a light receiving element to detect whether or not the image receiving unit 80 is in the accommodation portion 82. In addition, for example, a micro switch may be used as the attachment and detachment detection unit.

The accommodation portion 82 is provided with a locking mechanism and an unlocking mechanism that fix the image receiving unit 80 in the accommodation portion 82 to prevent the image receiving unit 80 from falling off and release the fixation, in addition to the contact sensor 84 or the non-contact sensor 90 as the attachment and detachment detection unit, which is not illustrated.

Further, as illustrated in FIG. 12A, a rotation shaft 92 that extends in the vertical direction is provided on the lower surface of the accommodation portion 82 so as to protrude. The rotation shaft 92 is supported by a bearing (not illustrated) that is provided at the other end of the arm 12. Therefore, the accommodation portion 82 and the image receiving unit 80 attached to the accommodation portion 82 can be rotated about an axis line R of the rotation shaft 92 with respect to the arm 12 while maintaining the confronting posture.

Further, a potentiometer 94 which is an example of a rotational position detection unit that detects a rotational position of the image receiving unit 80 is attached to the rotation shaft 92. The potentiometer 94 has a resistor (not illustrated) and a slider (not illustrated) that slides on the surface of the resistor as the rotation shaft 92 rotates. The potentiometer 94 detects a resistance value to detect the rotation angle of the rotation shaft 92 with respect to the arm 12.

Figure 13A:
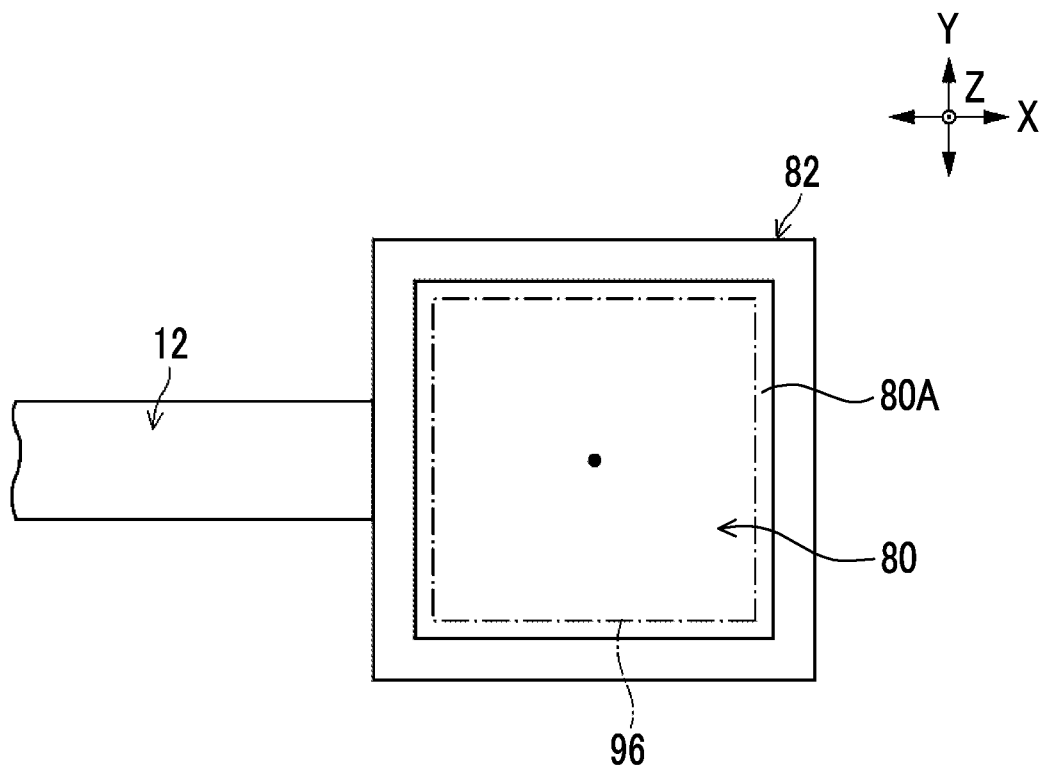
FIG. 13A is a plan view illustrating a case in which the image receiving unit of the radiography apparatus according to the third embodiment is at a reference rotational position.

For example, the rotational position where four sides of an irradiation field 96 of radiation are parallel to the corresponding four sides of the image receiving surface 80A, that is, the rotational position where four sides of the irradiation opening 34A (see FIG. 14) are parallel to the corresponding four sides of the image receiving surface 80A in a case in which the irradiation opening 34A is projected onto the image receiving surface 80A is a reference rotational position, as illustrated in FIG. 13A. Further, the rotation angle of the rotation shaft 92 (see FIG. 12A) at the reference rotational position is a reference angle.

In a case in which the image receiving unit 80 is at the reference rotational position, the irradiation field 96 of radiation does not deviate from the image receiving surface 80A and falls within the image receiving surface 80A. Even in a case in which the rotation shaft 92 is rotated at an interval of 90° (90°, 180°, and 270°) with respect to the reference angle, the image receiving unit 80 is at the reference rotational position.

Figure 13B:
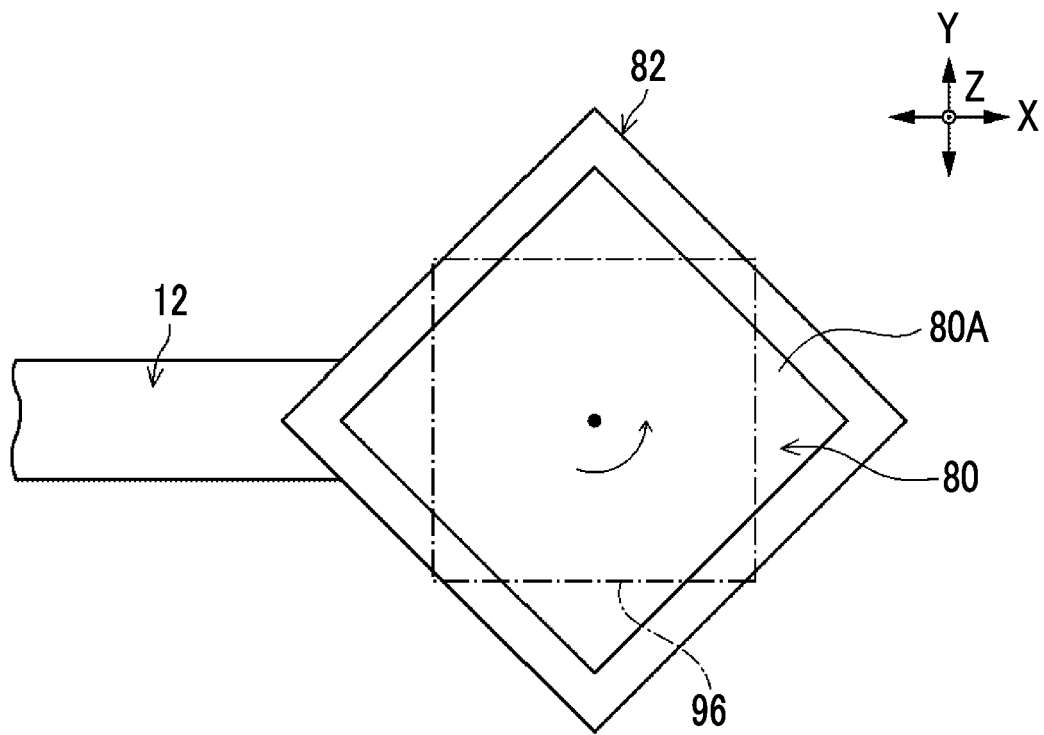
FIG. 13B is a plan view illustrating a case in which the image receiving unit of the radiography apparatus illustrated in FIG. 13A is at a rotational position other than the reference rotational position.

In contrast, as illustrated in FIG. 13B, in a case in which the rotation shaft 92 (see FIG. 12A) is rotated at an interval other than 90° with respect to the reference angle, the four sides of the irradiation field 96 of radiation are not parallel to the correspond four sides of the image receiving surface 80A. Therefore, the irradiation field 96 of radiation is likely to deviate from the image receiving surface 80A.

That is, the detection of the rotation angle of the rotation shaft 92 with respect to the reference angle by the potentiometer 94 illustrated in FIG. 12A makes it possible to detect whether or not the image receiving unit 80 is at the reference rotational position.

Even in a case in which the image receiving surface 80A of the image receiving unit 80 has a rectangular shape, similarly, the rotational position where the four sides of the irradiation field 96 of radiation are parallel to the corresponding four sides of the image receiving surface 80A is the reference rotational position. In a case in which the image receiving surface 80A has a rectangular shape and the rotation shaft is rotated by 90° with respect to the reference angle, the width of the image receiving surface 80A changes. In this case, the irradiation field 96 of radiation is adjusted by the irradiation field limiter 34 (see FIG. 14).

The rotational position detection unit is not limited to the potentiometer 94 as long as it has a function of detecting the rotational position of the accommodation portion 82 (and the image receiving unit 80) with respect to the arm 12. For example, as illustrated in FIG. 12B, a photo sensor 98 may be used as the rotational position detection unit.

In a case in which the photo sensor 98 is used as the rotational position detection unit, for example, a plurality of protrusions 100 that protrude outward in the radial direction of the rotation shaft 92 are provided at intervals of 90° on the outer peripheral surface of the rotation shaft 92. Then, the photo sensor 98 detects the presence or absence of the protrusion 100 to detect whether or not the accommodation portion 82 (and the image receiving unit 80) is at the reference rotational position.

As illustrated in FIG. 15, the control unit 88 receives the detection signals from the contact sensor 84 and the potentiometer 94 and determines whether or not the image receiving unit 80 is detached from the arm 12 and whether or not the rotational position of the image receiving unit 80 is the reference rotational position.

In a case in which it is determined that the image receiving unit 80 is detached from the arm 12 and in a case in which it is determined that the image receiving unit 80 is at a rotational position other than the reference rotational position, the control unit 88 transmits a control signal for prohibiting the moving image capture irradiation to the radiation tube 32 of the irradiation unit 18.

The control flow procedure of the control unit 88 according to this embodiment is the same as the control flow procedure of the control unit 28 according to the first embodiment. Here, in the control flow according to the first embodiment, the "start permission condition" for the capture of a moving image in Step S205 and the "continuation permission condition" for the capture of a moving image in Step S218 are that the rotation of the irradiation unit 18 with respect to the arm 12 is locked by the solenoid 44.

In this embodiment, the "start permission condition" and the "continuation permission condition" are that the solenoid 44 locks the rotation of the irradiation unit 18 with respect to the arm 12, the image receiving unit 80 is attached to the arm 12, and the image receiving unit 80 is at the reference rotational position.

That is, the control unit 88 prohibits (or stops) the moving image capture irradiation in a case in which it is determined that the image receiving unit 80 is detached from the arm 12 and in a case in which it is determined that the image receiving unit 80 is at a rotational position other than the reference rotational position, regardless of whether or not the rotation of the irradiation unit 18 is locked by the solenoid 44.

In the control flow, in a case in which the operator inputs a command to capture a still image, the control unit 88 permits the capture of a still image even in a state in which the capture of a moving image is prohibited or stopped. Therefore, for example, as illustrated in FIG. 14, even in a state in which the image receiving unit 80 is detached from the arm 12, it is possible to capture a still image.

Operation and Effect

According to the radiography apparatus 70 of this embodiment, the image receiving unit 80 is attachable to and detachable from the accommodation portion 82 fixed to the arm 12. The radiography apparatus 70 comprises the contact sensor 84 that detects whether or not the image receiving unit 80 is detached from the accommodation portion 82.

In a state in which the contact sensor 84 detects that the image receiving unit 80 is detached from the accommodation portion 82, the control unit 88 prohibits the irradiation unit 18 from performing the moving image capture irradiation. Therefore, it is possible to prevent radiation from being emitted from the irradiation unit 18 in a state in which the image receiving unit 80 is detached from the arm 12 and to suppress the emission of unnecessary radiation that does not contribute to the capture of a moving image.

Further, according to the radiography apparatus 70 of this embodiment, the image receiving unit 80 is rotatable with respect to the arm 12 in a state in which the image receiving unit 80 maintains the confronting posture. The radiography apparatus 70 comprises the potentiometer 94 that detects whether or not the image receiving unit 80 is at the reference rotational position.

Then, in a case in which the image receiving unit 80 is at a rotational position other than the reference rotational position, the control unit 88 prohibits the irradiation unit 18 from performing the moving image capture irradiation. Therefore, it is possible to prevent the irradiation unit 18 from emitting radiation in a state in which the four sides of the irradiation field 96 of radiation are not parallel to the corresponding four sides of the image receiving surface 80A and to suppress the emission of unnecessary radiation that does not contribute to the capture of a moving image.

Further, according to this embodiment, the control unit 88 permits the still image capture irradiation even in a case in which the moving image capture irradiation is prohibited. Therefore, it is possible to capture a still image even in a case in which the image receiving unit 80 is detached from the arm 12 and thus to improve convenience.

Other Embodiments

Examples of the embodiments of the present disclosure have been described above. However, the present disclosure is not limited to the above-described embodiments and various modifications and changes can be made without departing from the scope and spirit of the present disclosure. Further, the configurations of each of the above-described embodiments can be appropriately combined with each other.

For example, the irradiation unit 18 according to the third embodiment has the same configuration as the irradiation unit 18 according to the first embodiment and includes the solenoid 44 as the locking mechanism. However, the irradiation unit 18 according to the third embodiment may have the same configuration as the irradiation unit 58 according to the second embodiment and may comprise the posture detection unit 62.

In this case, in the third embodiment, the control unit 88 prohibits the moving image capture irradiation in a case in which it is determined that the image receiving unit 80 is detached from the arm 12 and in a case in which it is determined that the image receiving unit 80 is at a rotational position other than the reference rotational position, regardless of whether or not the posture detection unit 62 detects that the irradiation opening 34A is in the facing posture (or the confronting posture).

In the third embodiment, the image receiving unit 80 is attachable to and detachable from the arm 12 and is rotatable with respect to the arm 12. However, the image receiving unit 80 may only be attachable to and detachable from the arm 12 or may only be rotatable with respect to the arm 12.

That is, the image receiving unit 80 may be detachably attached to the accommodation portion 82 that is fixed to the arm 12 so as not to be rotatable. In this case, in a state in which the image receiving unit 80 is detached from the arm 12, the control unit 88 prohibits the irradiation unit 18 from performing the moving image capture irradiation, regardless of whether or not the rotation of the irradiation unit 18 is locked or whether or not the irradiation opening 34A is in the facing posture.

Further, the image receiving unit 80 may be fixed to the accommodation portion 82 that is rotatably supported by the arm 12 such that it is not detachable from the accommodation portion 82. In this case, the control unit 88 prohibits the irradiation unit 18 from performing the moving image capture irradiation in a case in which the image receiving unit 80 is at a rotational position other than the reference rotational position, regardless of whether or not the rotation of the irradiation unit 18 is locked or whether or not the irradiation opening 34A is in the facing posture.

In addition, in the third embodiment, the image receiving unit 80 is accommodated in the accommodation portion 82 provided at the other end of the arm 12. Therefore, the image receiving unit 80 is attachable to and detachable from the arm 12. However, a method for attaching and detaching the image receiving unit 80 to and from the arm 12 is not limited to the configuration according to the third embodiment.

Figure 16:
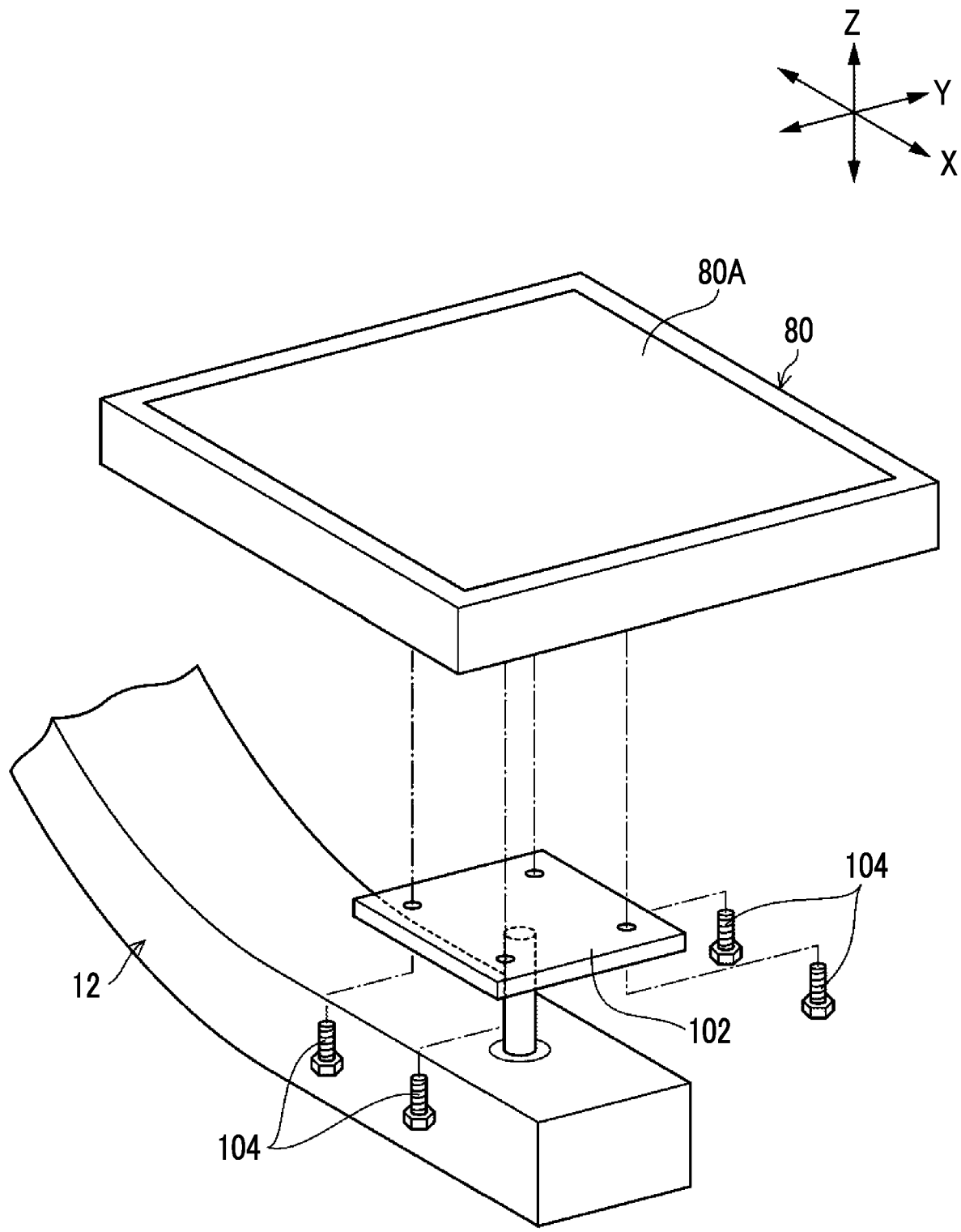
FIG. 16 is a partially exploded perspective view illustrating an image receiving unit of a radiography apparatus according to a modification example.

For example, as illustrated in FIG. 16, a base 102 is provided upright at the other end of the arm 12 and the image receiving unit 80 is fastened to the base 102 by a plurality of bolts 104 such that the image receiving unit 80 is attached to and detached from the arm 12. In this case, it is necessary to form a plurality of female screw holes (not illustrated) in the lower surface of the image receiving unit 80.

Further, in the first embodiment, the solenoid 44 is used as the locking mechanism. However, the locking mechanism is not limited to the solenoid 44 as long as a mechanism that can restrict the rotation of the irradiation unit 18 with respect to the arm 12 and release the restriction is provided.

In each of the above-described embodiments, the C-arm having a C-shape in a side view has been described as an example of the arm 12. However, a U-arm having a U-shape in a side view may be used. Similarly to the C-arm, the U-arm can hold, for example, the irradiation unit 18 and the image receiving unit 20 in a posture in which they face each other.

In addition, X-rays have been described as an example of the radiation. However, the present disclosure is not limited to the X-rays. For example, γ-rays may be used.

In each of the above-described embodiments, for example, the following various processors can be used as a hardware structure of processing units performing various processes, such as the control unit 28. The various processors include, for example, a CPU which is a general-purpose processor executing software to function as various processing units as described above, a programmable logic device (PLD), such as a field programmable gate array (FPGA), which is a processor whose circuit configuration can be changed after manufacture, and a dedicated electric circuit, such as an application-specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as the hardware structure.

Furthermore, specifically, an electric circuit (circuitry) obtained by combining circuit elements, such as semiconductor elements, can be used as the hardware structure of the various processors.

What is claimed is:

1. A radiography apparatus comprising:
   an irradiation unit having an irradiation opening through which radiation is emitted;
   an image receiving unit that has an image receiving surface receiving the radiation, which has been emitted from the irradiation unit and transmitted through a subject, and outputs a radiographic image of the subject;
   an arm that has one end at which the irradiation unit is provided and the other end at which the image receiving unit is capable of being supported in a posture in which the irradiation opening of the irradiation unit and the image receiving surface face each other and supports the irradiation unit so as to be rotatable in a direction in which orientation of the irradiation opening with respect to the image receiving surface is changed;
a locking mechanism that locks rotation of the irradiation unit with respect to the arm in a facing posture in which the irradiation opening and the image receiving surface face each other; and
a control unit that is capable of directing the irradiation unit to perform moving image capture irradiation in which the irradiation unit continuously emits the radiation to capture a moving image of the subject, permits the moving image capture irradiation in a state in which the rotation of the irradiation unit is locked by the locking mechanism, and prohibits the moving image capture irradiation in a state in which the rotation is unlocked by the locking mechanism.

2. The radiography apparatus according to claim 1, wherein the facing posture is a confronting posture in which a central axis of a beam of the radiation that spreads in a cone shape from a focus of the irradiation unit through the irradiation opening is aligned with a normal line to the image receiving surface.

3. The radiography apparatus according to claim 1, wherein, in a case in which a direction in which the irradiation unit and the image receiving unit are provided with respect to the arm is a front side and an arm side is a rear side in a side view of the arm, the irradiation unit is rotated with respect to the arm such that the orientation of the irradiation opening is changed in a front-rear direction.

4. The radiography apparatus according to claim 1, wherein control to prohibit the moving image capture irradiation by the control unit includes at least one of control to prohibit a start of the moving image capture irradiation in a case in which there is a command to start the moving image capture irradiation or control to stop the moving image capture irradiation while the moving image is being captured.

5. The radiography apparatus according to claim 4, further comprising:
a warning unit that issues a warning in at least one of a case in which the control unit prohibits the start of the moving image capture irradiation or a case in which the control unit stops the moving image capture irradiation while the moving image is being captured.

6. The radiography apparatus according to claim 1, wherein the control unit is capable of directing the irradiation unit to perform still image capture irradiation in which the irradiation unit emits the radiation for a shorter time than in the moving image capture irradiation to capture a still image of the subject, in addition to the moving image capture irradiation, and
the control unit permits the still image capture irradiation even in a case in which the moving image capture irradiation is prohibited.

7. The radiography apparatus according to claim 1, wherein the image receiving unit is attachable to and detachable from the arm,
the radiography apparatus further comprises an attachment and detachment detection unit that detects whether or not the image receiving unit is detached from the arm, and
the control unit prohibits the irradiation unit from performing the moving image capture irradiation in a state in which the image receiving unit is detached from the arm, regardless of whether or not the rotation of the irradiation unit by the locking mechanism is locked or whether or not the posture detection unit detects that the irradiation opening is in the facing posture.

8. The radiography apparatus according to claim 3, wherein each of the irradiation opening and the image receiving surface has a rectangular shape,
the image receiving unit is rotatable with respect to the arm while maintaining the confronting posture,
the radiography apparatus further comprises a rotational position detection unit that detects at least four rotational positions of the image receiving unit where, in a case in which the irradiation opening is projected onto the image receiving surface, four sides of the irradiation opening are parallel to corresponding four sides of the image receiving surface, the at least four rotational positions being set at intervals of 90°,
the control unit prohibits the irradiation unit from performing the moving image capture irradiation in a case in which the image receiving unit is at a rotational position other than the four rotational positions, regardless of whether or not the rotation of the irradiation unit by the locking mechanism is locked or whether or not the posture detection unit detects that the irradiation opening is in the confronting posture, and
the facing posture is a confronting posture in which a central axis of a beam of the radiation that spreads in a cone shape from a focus of the irradiation unit through the irradiation opening is aligned with a normal line to the image receiving surface.

9. A method for controlling a radiography apparatus including an irradiation unit having an irradiation opening through which radiation is emitted, an image receiving unit that has an image receiving surface receiving the radiation, which has been emitted from the irradiation unit and transmitted through a subject, and outputs a radiographic image of the subject, an arm that has one end at which the irradiation unit is provided and the other end at which the image receiving unit is capable of being supported in a posture in which the irradiation opening of the irradiation unit and the image receiving surface face each other and supports the irradiation unit so as to be rotatable in a direction in which orientation of the irradiation opening with respect to the image receiving surface is changed, and a control unit that is capable of directing the irradiation unit to perform moving image capture irradiation in which the irradiation unit continuously emits the radiation to capture a moving image of the subject, the method comprising:
allowing the control unit to perform at least one of first control to permit the moving image capture irradiation in a state in which rotation of the irradiation unit is locked by a locking mechanism that locks the rotation of the irradiation unit with respect to the arm in a facing posture in which the irradiation opening and the image receiving surface face each other and to prohibit the moving image capture irradiation in a state in which the rotation is unlocked by the locking mechanism or second control to permit the moving image capture irradiation in a state in which a posture detection unit that detects whether or not the irradiation opening is in a facing posture in which the irradiation opening faces the image receiving surface detects that the irradiation opening is in the facing posture and to prohibit the moving image capture irradiation in a state in which the posture detection unit does not detect that the irradiation opening is in the facing posture.

10. The radiography apparatus according to claim 3, wherein the control unit is capable of directing the irradiation unit to perform still image capture irradiation in which the irradiation unit emits the radiation for a shorter time than in the moving image capture irradiation to capture a still image of the subject, in addition to the moving image capture irradiation, and the control unit permits the still image capture irradiation even in a case in which the moving image capture irradiation is prohibited.

11. The radiography apparatus according to claim 6, wherein the image receiving unit is attachable to and detachable from the arm, the radiography apparatus further comprises an attachment and detachment detection unit that detects whether or not the image receiving unit is detached from the arm, and the control unit prohibits the irradiation unit from performing the moving image capture irradiation in a state in which the image receiving unit is detached from the arm, regardless of whether or not the rotation of the irradiation unit by the locking mechanism is locked or whether or not the posture detection unit detects that the irradiation opening is in the facing posture.

* * * * *